(12) United States Patent
Cui et al.

(10) Patent No.: US 8,189,204 B2
(45) Date of Patent: May 29, 2012

(54) SURFACE WAVE ENABLED DARKFIELD APERTURE

(75) Inventors: Xiquan Cui, Pasadena, CA (US); Xin Heng, Somerville, MA (US); Changhuei Yang, Pasadena, CA (US); Axel Scherer, Laguna Beach, CA (US); Demetri Psaltis, Lausanne (CH); Guoan Zheng, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 12/792,059

(22) Filed: Jun. 2, 2010

(65) Prior Publication Data

US 2011/0075254 A1     Mar. 31, 2011

Related U.S. Application Data

(63) Continuation-in-part of application No. 11/743,581, filed on May 2, 2007, now Pat. No. 7,768,654.

(60) Provisional application No. 60/796,997, filed on May 2, 2006, provisional application No. 60/796,996, filed on May 2, 2006, provisional application No. 61/183,868, filed on Jun. 3, 2009, provisional application No. 61/345,018, filed on May 14, 2010.

(51) Int. Cl.
*G01B 9/02* (2006.01)

(52) U.S. Cl. ....................................................... 356/521

(58) Field of Classification Search .................... 356/521
See application file for complete search history.

(56) References Cited

U.S. PATENT DOCUMENTS

| | | | |
|---|---|---|---|
| 5,196,350 | A | 3/1993 | Backman et al. |
| 5,426,505 | A | 6/1995 | Geiser et al. |
| 6,858,436 | B2 | 2/2005 | Zenhausern et al. |
| 7,250,598 | B2 | 7/2007 | Hollingsworth et al. |
| 7,751,048 | B2 | 7/2010 | Yang et al. |
| 7,768,654 | B2 | 8/2010 | Cui et al. |
| 7,773,227 | B2 | 8/2010 | Yang et al. |
| 7,982,883 | B2 | 7/2011 | Cui et al. |
| 2004/0190116 | A1* | 9/2004 | Lezec et al. ........... 359/298 |
| 2005/0271548 | A1 | 12/2005 | Yang et al. |
| 2007/0172745 | A1 | 7/2007 | Smith |
| 2007/0207061 | A1 | 9/2007 | Yang et al. |
| 2007/0258096 | A1 | 11/2007 | Cui et al. |
| 2009/0276188 | A1 | 11/2009 | Cui et al. |
| 2010/0195873 | A1 | 8/2010 | Cui et al. |
| 2010/0309457 | A1 | 12/2010 | Cui et al. |

(Continued)

OTHER PUBLICATIONS

Aigouy, L., et al., "Near-field analysis of surface waves launched at nanoslit apertures," Physical Review Letters, vol. 98, pp. 153902-1-153902-4 (Apr. 2007).

(Continued)

*Primary Examiner* — Tarifur Chowdhury
*Assistant Examiner* — Jonathan Hansen
(74) *Attorney, Agent, or Firm* — Sheila Martinez-Lemke

(57) ABSTRACT

Embodiments of the present invention relate to a surface wave enabled darkfield aperture structure comprising an aperture layer, a aperture in the aperture layer and a plurality of grooves around the aperture. The aperture layer has a first and second surface. The plurality of grooves is in the first surface. A surface wave propagates along at least the first surface. The plurality of grooves is configured to generate a darkfield at the aperture by modifying the surface wave to cancel out direct transmission of a uniform incident light field received by the aperture.

15 Claims, 21 Drawing Sheets

U.S. PATENT DOCUMENTS

2011/0063623 A1 3/2011 Cui et al.

OTHER PUBLICATIONS

Arnison, M.R., et al., "Linear phase imaging using differential interference contrast microscopy," Journal of Microscopy, vol. 214, Pt. 1, pp. 7-12 (Apr. 2004).
Bouwkamp, C.J., "Diffraction theory," Reports on Progress in Physics XVIII, pp. 35-100 (1954).
Chen, L., et al. "Role of radiation and surface plasmon polaritons in the optical interactions between a nano-slit and a nano-groove on a metal surface," Optics Express, vol. 14, pp. 12629-12636 (2006).
Cui, Xiquan, et al., "Portable optical microscope-on-a-chip," P{roc. of SPIE, vol. 6095, pp. 609509-1-609509-8 (Jan. 2006).
Cui, Xiquan, et al., "Quantitative differential interference contrast microscopy based on structured-aperture interference," Applied Physics Letters, vol. 93, pp. 091113-1-091113-3 (2008).
Cui, Xiquan, et al., "Slanted hole array beam profiler (SHArP)—a high-resolution portable beam profiler based on a linear aperture array," Optics Letters, vol. 31, No. 21, pp. 3161-3163 (Nov. 2006).
Doyle, Patrick S., et al., "Self-assembled magnetic matrices for DNA separation chips," Science, vol. 295, No. 5563, p. 2237 (Mar. 2002).
Drezet, Aurelien, et al., "Miniature plasmonic wave plates," Physical Review Letters, vol. 101, pp. 43902-1-43902-4 (Jul. 2008).
Dunn, et al., "Introduction to Confocal Microscopy," available from MicroscopyU at http://www.microscopyu.com/articles/confocal (2007).
Ebbesen, T.W., et al., "Extraordinary optical transmission through sub-wavelength hole arrays," Nature, vol. 391 (6668), pp. 667-669 (Feb. 1998).
Fu, Anne Y., et al., "A microfabricated fluorescence-activated cell sorter," Nature Biotechnology, vol. 17, pp. 1109-1111 (Nov. 1999).
Garcia De Abajo, F. J., "Light transmission through a single cylindrical hole in a metallic film," Optics Express, vol. 10, No. 25, pp. 1475-1484 (2002).
Gay, G., et al., "The optical response of nanostructured surfaces and the composite diffracted evanescent wave model," Nature Physics, vol. 2, pp. 262-267 (Mar. 2006).
Gbur, Greg, et al., "Achieving superresolution in near-field optical data readout systems using surface plasmons," Applied Physics Letters, vol. 87, Issue 19, pp. 191109-1-191109-3 (2005).
Heng, Xin, et al., "Characterization of light collection through a subwavelength aperture from a point source," Optics Express, vol. 14, pp. 10410-10425 (2006).
Heng, Xin, et al "Optofluidic Microscope, a miniature microscope on a chip," 9th International Conference on Miniaturized Systems for Chemistry and Life Sciences (µTAS) (2005).
Heng, Xin, et al., "Optofluidic Microscopy—a method for implementing a high resolution optical microscope on a chip," Lab Chip, vol. 6, pp. 1274-1276 (2006).
Lalanne, P., and Hugonin, J. P., "Interaction between optical nano-objects at metallo-dielectric interfaces," Nature Physics, vol. 2, pp. 551-556 (Aug. 2006).
Laux, Eric, et al., "Plasmonic photon sorters for spectral and polarimetric imaging," Nature Photonics, vol. 2, pp. 161-164 (Feb. 2008).
Leen, Brian J., et al.,"Improved focused ion beam fabrication of near-field apertures using a silicon nitride membrane," Optics Letters, vol. 33, No. 23, pp. 2827-2829 (2008).
Lezec, Henri J., et al., "Beaming Light from a Subwavelength Aperture," Science, vol. 297, No. 5582, pp. 820-822 (2002).
Lezec, Henri J., and Thio, Tineke, "Diffracted evanescent wave model for enhanced and suppressed optical transmission through subwavelength hole arrays," Optics Express, vol. 12, No. 16, pp. 3629-3651 (Aug. 2004).

Liu, Haitao, and Lalanne, Philippe, "Microscopic theory of the extraordinary optical transmission," Nature, vol. 452, pp. 728-731 (Apr. 2008).
Liu, Shaorong, "A microfabricated hybrid device for DNA sequencing," Electrophoresis 2003, vol. 24(21), pp. 3755-3761 (2003).
Minakawa, Kyosuke, et al.,"Microchamber Device Equipped with Complementary Metal Oxide Semiconductor Optical Polarization Analyzer Chip for Micro Total Analysis System," Jpn. J. Appl. Phys., vol. 48, pp. 04C192-1-04C192-5 (2009).
Murphy, et al., "Differential Interference Contrast (DIC)," available from Nikon MicrocopyU at http://www.microscopyu.com/articles/dic/dicindex.html (2007).
NG, Ren, et al., "Light field photography with a hand-held plenoptic camera," Stanford Tech Report CSTR Feb. 2005, vol. 2, pp. 1-11.
Pacifici, Dominico, et al., "Quantitative determination of optical transmission through subwavelength slit arrays in Ag films: Role of surface wave interference and local coupling between adjacent slits," Physical Review B, vol. 77, pp. 115411-1-115411-5 (2008).
Pacifici, Dominico, et al., "All-optical modulation by plasmonic excitation of CdSe quantum dots," Nature photonics, vol. 1, pp. 402-406 (Jul. 2007).
Pacific!, Dominico., et al., "Universal optical transmission features in periodic and quasiperiodic hole arrays," Optics Express, vol. 16, No. 12, pp. 9222-9238 (Jun. 2008).
Schouten, H. F., et al., "Plasmon-assisted two-slit transmission: Young's experiment revisited," Physical Review Letters, vol. 94, pp. 053901-1-053901-4 (Feb. 2005).
Schwiegerling, Jim, and Neal, Daniel,"Historical development of the Shack-Hartmann wavefront sensor," in Robert Shannon and Roland Shack: Legends in Applied Optics, edited by J. E. Harvey and R. B. Hooker_SPIE, Bellingham, WA, pp. 132-139 (2005).
Shi, Xiaolei, et al., "Ultrahigh light transmission through a C-shaped nanoaperture," Optics letters, vol. 28, No. 15, pp. 1320-1322 (Aug. 2003).
Tegenfeldt, Jonas O., et al., "Micro- and nanofluidics for DNA analysis," Analytical and Bioanalytical Chemistry, 378(7), pp. 1678-1692 (Mar. 2004).
Tegenfeldt, Jonas O., et al., "Near-field Scanner for Moving Molecules," Physical review letters, 86(7), vol. 86, No. 7, pp. 1378-1381 (Feb. 2001).
Thio, Tineke, et al., "Enhanced light transmission through a single subwavelength aperture," Opt. Lett., vol. 26, No. 24pp. 1972-1974 (Dec. 2001).
Thio, Tineke, et al., "Giant optical transmission of sub-wavelength apertures: physics and applications," Nanotechnology, vol. 13, pp. 429-432 (2002).
Tokeshi, Manabu, et al., "Chemical processing on microchips for analysis, synthesis, and bioassay," Electrophoresis, vol. 24, No. 21, pp. 3583-3594 (2003).
Trau, Dieter, et al., "Genotyping on a complementary metal oxide semiconductor silicon polymerase chain reaction chip with integrated DNA microarray," Analytical Chemistry, vol. 74, No. 13, pp. 3168-3173 (2002).
Ung, Bora, and Sheng, Yunlong, "Optical surface waves over metallo-dielectric nanostructures: Sommerfeld integrals revisited," Optics Express, vol. 16, No. 12, pp. 9073-9086 (Jun. 2008).
Yu, Nanfang, et al., "Semiconductor lasers with integrated plasmonic polarizers," Applied Physics Letters, vol. 94, pp. 151101-1-151101-3 (2009).
Zheng, Guoan, et al., "Surface-wave-enabled darkfield aperture: A method for suppressing background during weak signal detection," Proc Natl Acad Sci U S A, vol. 107, No. 20, pp. 9043-9048 (May 2010).
Wikipedia, "Surface Plasmon," last modified Apr. 4, 2010.

* cited by examiner

US 8,189,204 B2

SURFACE WAVE ENABLED DARKFIELD APERTURE

CROSS-REFERENCES TO RELATED APPLICATIONS

This is a continuation-in-part application of U.S. patent application Ser. No. 11/743,581 (now U.S. Pat. No. 7,768,654), filed on May 2, 2007, which is a non-provisional of and claims priority to U.S. provisional applications 60/796,997 and 60/796,996 filed on May 2, 2006. This application is also a non-provisional of and claims priority to U.S. provisional applications 61/183,868, filed on Jun. 3, 2009 and 61/345,018 filed on May 14, 2010. All of these applications are hereby incorporated by reference in their entirety for all purposes.

This non-provisional application is related to the following co-pending and commonly-assigned patent applications, which are hereby incorporated by reference in their entirety for all purposes:

U.S. patent application Ser. No. 11/125,718 entitled "Optofluidic Microscope Device" filed on May 9, 2005, now U.S. Pat. No. 7,773,227.
U.S. patent application Ser. No. 11/686,095 entitled "Optofluidic Microscope Device" filed on Mar. 14, 2007, now U.S. Pat. No. 7,751,048.
U.S. patent application Ser. No. 12/398,050 entitled "Optofluidic Microscope Device with Photosensor Array" filed on Mar. 4, 2009.
U.S. patent application Ser. No. 12/435,165 entitled "Quantitative Differential Interference Contrast (DIC) Microscopy and Photography Based on Wavefront Sensors" filed on May 4, 2009, now U.S. Pat. No. 8,039,776.
U.S. patent application Ser. No. 12/690,952 entitled "Quantitative Differential Interference Contrast (DIC) Microscopy and its Computed Depth Sectioning Ability" filed on Jan. 21, 2010.

The following non-provisional patent application is being filed on the same day and is hereby incorporated by reference in its entirety for all purposes: U.S. patent application Ser. No. 12/792,177 filed on Jun. 2, 2010, entitled "Wavefront Imaging Sensor".

STATEMENT REGARDING FEDERALLY SPONSORED RESEARCH AND DEVELOPMENT

The U.S. Government has certain rights in this invention pursuant to Grant No. HR0011-04-1-0032 awarded by DARPA and pursuant to Grant No. EB008867 awarded by NIH.

BACKGROUND OF THE INVENTION

Differential Interference Contrast (DIC) Microscopes

A major problem of imaging transparent specimens with conventional microscopes is that it can be difficult to elicit contrast, because the imaging technique is solely based on the amplitude information of the sampling light. This difficulty can be especially problematic for examining transparent or nearly transparent biological specimens. Phase information, if measured, can improve the imaging contrast dramatically. Conventional differential interference contrast (DIC) microscopy performs admirably in this respect by rendering excellent phase contrast in these biological specimens, and is widely used in biology and clinical laboratories.

DIC microscopes are beam-shearing interference systems. An example of a conventional DIC microscope can be found in Murphy, Schwartz, Salmon, Spring, Parry-Hill, Sutter, and Davidson, Differential Interference Contrast (DIC), 2007, available from Nikon MicroscopyU at http://www.microscopyu.com/articles/dic/dicindex.html, which is hereby incorporated by reference in its entirety for all purposes. In DIC microscopes, a reference beam is sheared by a very small distance with respect to a sample beam. The phase difference between the reference beam and the sample beam after they pass two adjacent spots of the specimen provides the differential phase contrast of the specimen. Since DIC microscopy is an interference-based technique, it can distinguish minuscule amounts of phase differences and identify small changes in the sample's refractive index.

Prior art DIC microscopes have some disadvantages. Firstly, prior art DIC microscopes are very expensive instruments, as many complicated and expensive optical components are required to manipulate the light. Secondly, the lateral resolution of current DIC microscopes is determined by the spot size of the objective lens of the DIC microscope, which has a diffraction limit. The small sheared distance between the reference beam and the sample beam is usually tuned to be slightly smaller than this spot size.

Microfluidics

Recent developments in microfludics have brought forth a variety of new devices that can potentially revolutionize traditional biomedical and chemical experiments. Examples of microfluidic devices can be found in Fu, A. Y., et al., "A microfabricated fluorescence-activated cell sorter, Nature Biotechnology," 1999, 17(11), pp. 1109-1111, Tai, Y. C., et al., "Integrated micro/nano fluidics for mass-spectrometry protein analysis," International Journal of Nonlinear Sciences and Numerical Simulation, 2002, 3(3-4), pp. 739-741, Tokeshi, M., et al., "Chemical processing on microchips for analysis, synthesis, and bioassay," Electrophoresis, 2003, 24(21): pp. 3583-3594, Doyle, P. S., et al., "Self-assembled magnetic matrices for DNA separation chips," Science, 2002, 295(5563), pp. 2237-2237, Trau, D., et al., "Genotyping on a complementary metal oxide semiconductor silicon polymerase chain reaction chip with integrated DNA microarray, Analytical Chemistry," 2002, 74(13), pp. 3168-3173, and Liu, S. R., "A microfabricated hybrid device for DNA sequencing," Electrophoresis, 2003, 24(21), pp. 3755-3761, which are hereby incorporated by reference in their entirety for all purposes. Another such device is the optofluidic microscope (OFM) described in U.S. patent application Ser. No. 11/686,095, filed on Mar. 14, 2007, by Changhuei Yang and Demetri Psaltis, entitled OPTOFLUIDIC MICROSCOPE DEVICE, which is hereby incorporated by reference in its entirety for all purposes. The OFM fuses the advantage of optical imaging in providing high resolution and the advantages of microfluidics, such as low cost and high throughput. Further, OFM's application in nematode imaging and phenotyping has been reported in Heng, X., et al., "Optofluidic microscope, a miniature microscope on a chip," 9th International Conference on Miniaturized Systems for Chemistry and Life Sciences (µTAS), 2005, which is hereby incorporated by reference in its entirety for all purposes.

FIGS. 1A and 1B are schematic drawings an OFM device having a body that forms a fluid channel. An object is passing through the fluid channel generally in the flow direction. The body includes an aperture layer having an aperture array of light transmissive regions (e.g., apertures, slits, etc.). The aperture layer is located adjacent to the light detector layer having an array of light detecting elements. The aperture array is oriented at a small angle β relative to the fluid channel (FIG. 1B). As an object passes over the aperture array, light detecting elements detect light through the light transmissive regions. The sensor of a processor communicating with the sensor generates time-varying data in the form of a line scan which can be compiled into an image of the object.

FIG. 2(a) illustrates an image of a wild-type *C. elegans* larvae at the first larval stage that was generated by an OFM device. FIG. 2(b) is an OFM generated image of a dpy-24 mutant that was generated by an OFM device. FIG. 2(c) illustrates the aspect ratio of wild-type larvae and dpy-24 mutants that was generated by an OFM device.

In many cases, the light transmissive regions in the OFM device may be of a small size due to the compactness of the OFM device. In these cases, light detector may detect a weak signal. The reduced optical transmission through small apertures is described in Bouwkamp, C. J., "Diffraction theory," Reports on Progress in Physics XVIII, 1954, p. 35 and de Abajo, F., "Light transmission through a single cylindrical hole in a metallic film," Optics Express, 2002, 10(25), pp. 1475-1484, which are hereby incorporated by reference in their entirety for all purposes. The weak transmission signal can be buried in noise. Although strong illumination from strong sources such as powerful lasers can help to increase the total transmission through small light transmissive regions, high-intensity light may also have adverse effects on the biological specimens.

Darkfield Imaging

The ability of an optical sensor to detect light signals, especially weak light signals, can be limited by the presence of a bright background. This limitation is described in R. Narayanaswamy and O. Wolfbeis, "Optical sensors: industrial, environmental and diagnostic applications," Springer Berlin, 2004, and G. C. Cox, "Optical imaging techniques in cell biology," Boca Raton: CRC/Taylor & Francis, 2007, which are hereby incorporated by reference in their entirety for all purposes. As such, pre-detection background suppression providing a darkfield can be important in the detection of light signals. The benefit of a darkfield image can be appreciated by drawing an analogy to the visibility of stars in the night and their apparent absence during the day—the absence of the bright background can significantly enhance the relative contrast of the light fields.

Darkfield imaging has numerous advantages and applications. For example, darkfield imaging of biological specimens can be advantageous because the outlines of specimens tend to be show up prominently in darkfield images as bright lines delineating the objects and because the interior structures of specimens show up well for similar reasons. In some cases, the increased contrast provided by darkfield imaging can eliminate the need for staining specimens, which could be vitally useful for certain time critical medical procedures such as pathological examination of resected tissue samples during surgery.

Prior darkfield imaging devices such as conventional darkfield microscopes use complex and expensive components to generate a darkfield image. For example, FIG. 3(a) is a schematic drawing of portions of a conventional darkfield microscope having a cardioid darkfield condenser. The condenser is structured so that light emerging from is incident at large angles on the object. The objective on the opposite side of the object is selected so that the numerical aperture is sufficiently small to ensure that the objective will not collect the illumination light field in the absence of the object. The optics process the scattered or diffracted light due to the presence of the object, to render a darkfield image. FIG. 3(b) is a darkfield image of *Chlamydomonas* generated using the conventional darkfield microscope. FIG. 3(c) is a bright field image of *Chlamydomonas* generated using a bright field microscope.

Conventional darkfield microscopes are also difficult to operate and can require extensive training. Since the illumination light field must be excluded from the collection aperture of the objective, it precludes the use of high numerical aperture objectives. Additionally, using conventional darkfield microscopes requires familiarity with their working principles, and the positioning of condenser, sample, and objective demands precision.

BRIEF SUMMARY OF THE INVENTION

Embodiments of the present invention relate to darkfield sensing and imaging. More specifically, certain embodiments relate to a surface wave enabled darkfield aperture for destructively interfering with pre-detection light under a uniform incident light field, sensors that employ SWEDAs, and methods of fabricating SWEDAs.

In one embodiment, a surface wave enabled darkfield aperture (SWEDA) structure comprises an aperture layer having a first surface and a second surface. A surface wave propagates along the first surface. The SWEDA structure further comprises an aperture in the aperture layer and a plurality of grooves in the first surface around each aperture. The plurality of grooves is configured to generate a darkfield at the aperture by modifying the surface wave to cancel out direct transmission of a uniform incident light field received by the aperture. In one case, the SWEDA structure is also configured to pass light of a non-uniform light field through the aperture. In another case, the aperture and the plurality of grooves are configured to modify the direct transmission based on a degree if polarity of the uniform light field.

In another embodiment, a surface wave enabled darkfield aperture (SWEDA) sensor comprises an aperture layer having a first surface and a second surface. A surface wave propagates along the first surface of the aperture layer. The SWEDA sensor further comprises a plurality of apertures in the aperture layer and a plurality of grooves in the first surface around each corresponding aperture. The plurality of grooves configured to generate a darkfield at the corresponding aperture by modifying the surface wave to cancel out direct transmission of a uniform incident light field received by the aperture. The SWEDA sensor further comprising a light detector adapted to detect light passing through the apertures.

These and other embodiments of the invention are described in further detail below.

DETAILED DESCRIPTION OF THE INVENTION

Figure 1A:
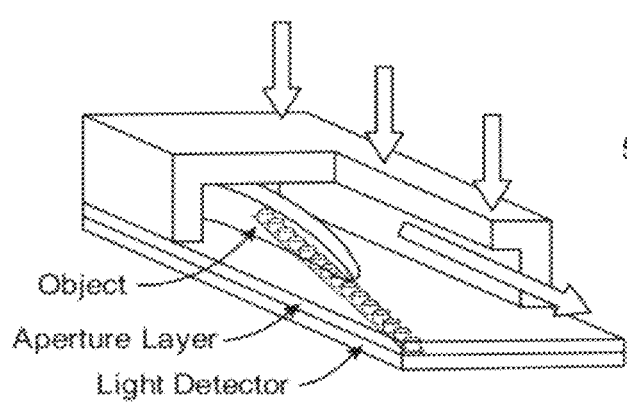
FIGS. 1A and 1B are schematic drawings of an optofluidic microscope device comprising an opaque or semi-opaque film with an array of apertures.
Figure 1B:
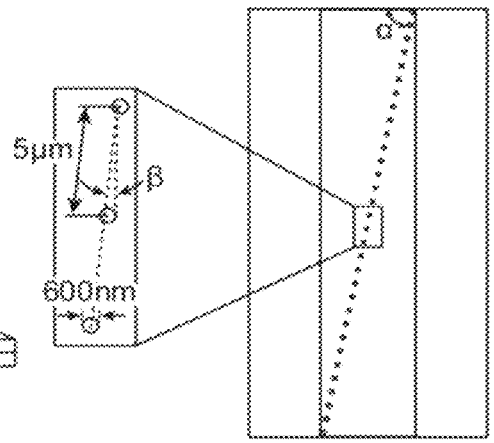

Some embodiments of the invention provide an improved DIC microscope. Other embodiments provide a SWEDA structure having a plurality of grooves around a darkfield aperture that is designed to create a darkfield by cancelling out background light and/or enhancing transmission through an object (specimen). In some cases, the SWEDA structure can also modify the transmission based on the polarity of the light in the incident light field so that the SWEDA structure can be used as a polarity sensor.

I. Differential Interference Contrast (DIC) Microscope/ Light Field Profiler Based on Young's Interference FIGS. 4A and 4B shows the configuration of a DIC microscope based on Young's interference and the operating principle, in accordance with one or more embodiments of the invention.

The DIC microscope 300 consists of two main parts for a Young's interference setup based on two apertures 306 and 308 (i.e., in metal film 309) and a light detector 312 (e.g., CCD [charge-coupled device], CMOS [complimentary metal-oxide semiconductor], PSD [photo-sensitive light detector], etc.).

Aperture 1 306 may be used to sample the reference beam from the specimen 304 (object), and aperture 2 308 may be used to sample the sample beam from the specimen 304. If the reference beam and the sample beam pass a homogenous region of the specimen 304, the reference beam and the sample beam carry the same phase. When the reference and sample beams exit from the two apertures 306 and 308, the light intensity distribution 314 of their Young's interference 310 is centered on the light detector 312 (as illustrated in FIG. 4A). However, if the reference beam and the sample beam pass different features in the specimen 304 (i.e., as illustrated by the reference beam passing over the nucleus in FIG. 4B), the beams will carry different phases. Accordingly, when the beams exit from the two apertures 306 and 308, the light intensity distribution of their Young's interference 310 is shifted on the light detector 312. The offset is directly related to the phase difference between the reference beam and the sample beam.

As described herein, Young's interference is used to determine the phase in accordance with $$\Delta \phi \approx \frac{2\pi}{\lambda} \frac{a}{D} x,$$

wherein D is distance 320, a is distance 318, and x is the displacement with respect to the center of the apertures 304, 306.

From the data of light detector 312, the information of the differential phase contrast of the specimen 304 can be easily retrieved. In addition, the amplitude of the sample 304 transmission at that location can be computed by simply summing up all of the signals from the light detector array 312.

Figure 4:
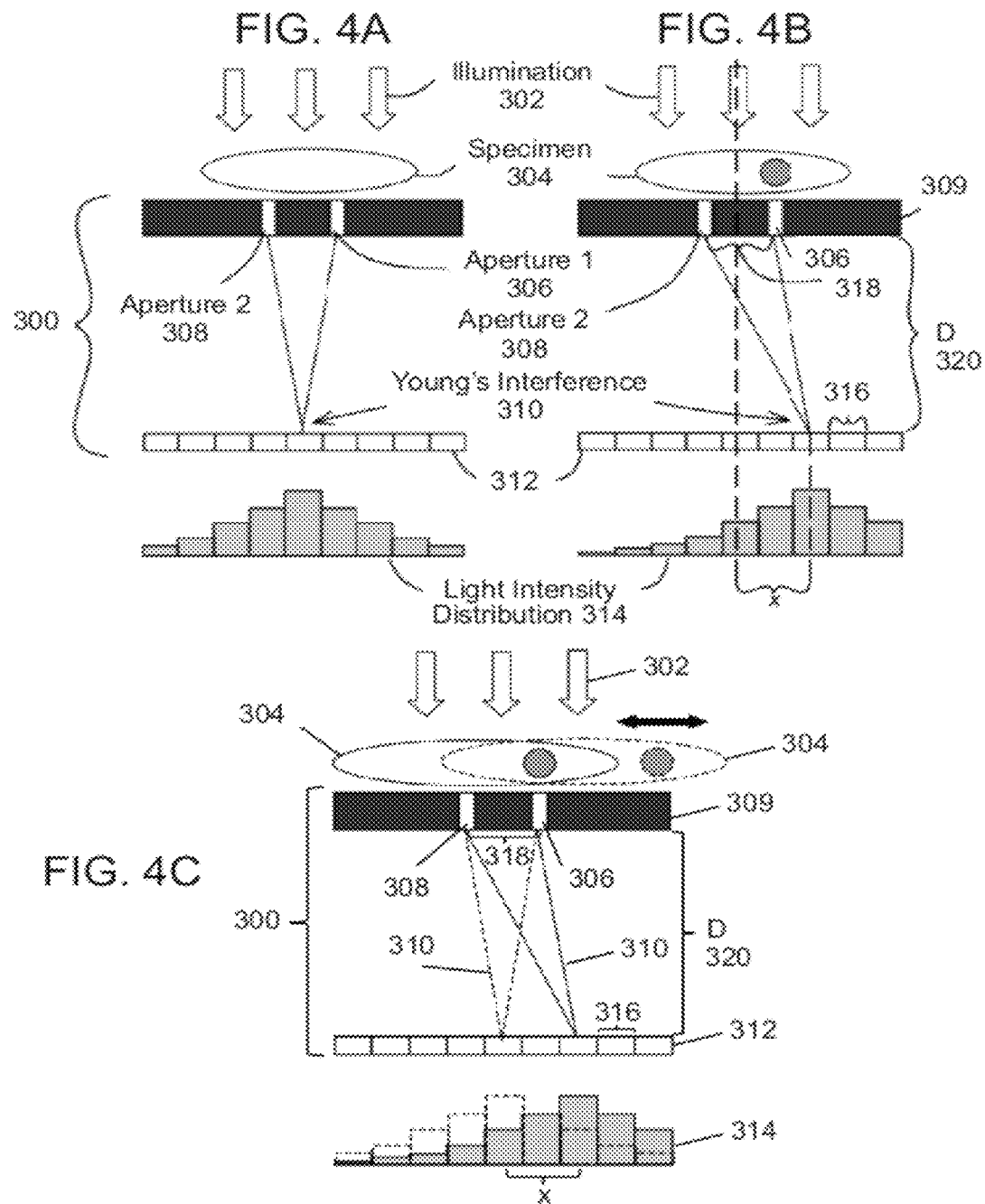
FIGS. 4A and 4B are schematic drawings of a DIC microscope, in accordance with one or more embodiments of the invention.
FIG. 4C is a schematic drawing of a DIC microscope scanning a specimen, in accordance with one or more embodiments of the invention.

To get all of the information of differential phase contrast from the whole specimen 304, one may either scan the DIC microscope 300 across the specimen 304 or scan the specimen 304 across the DIC microscope 300. FIG. 4 illustrates such a scanning of the specimen 304 in accordance with one or more embodiments of the invention.

Figure 5:
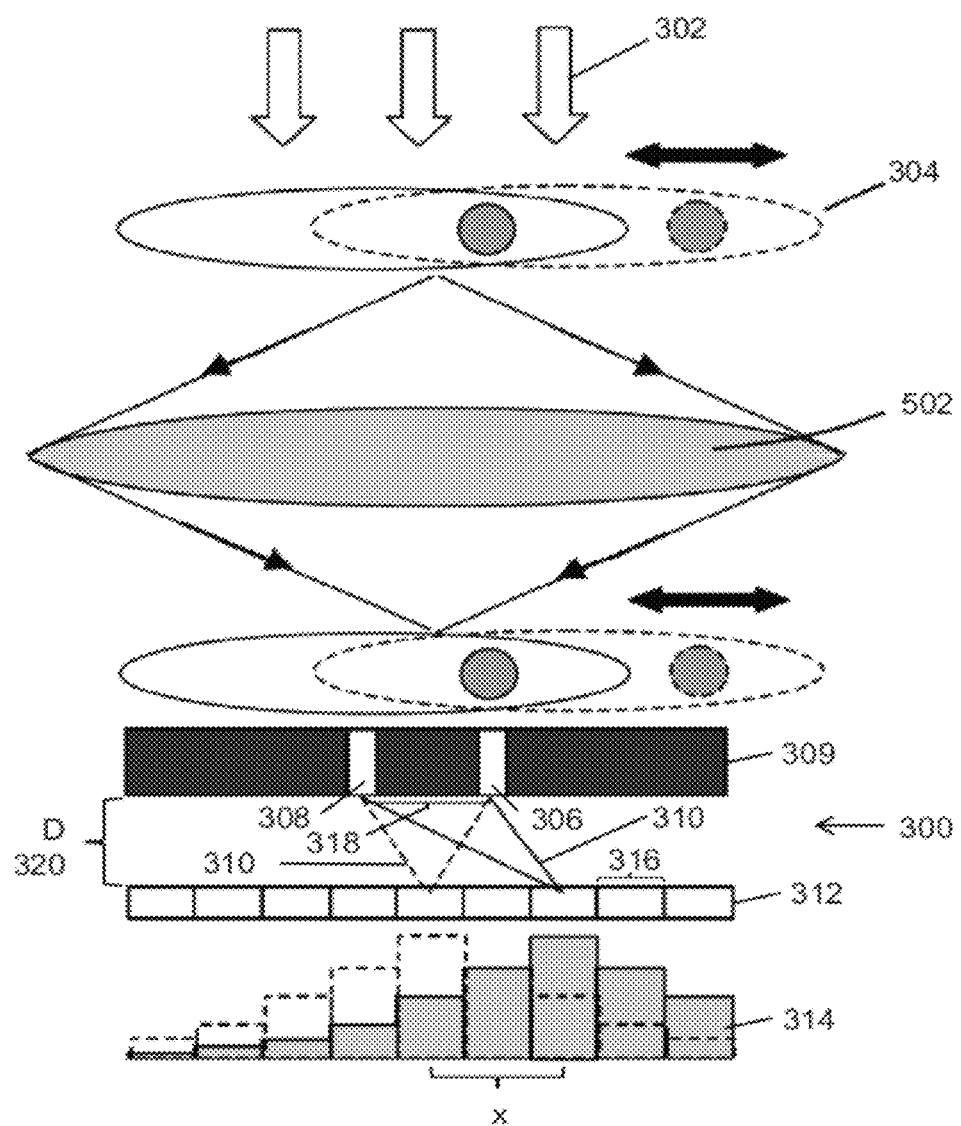
FIG. 5 is a schematic drawing of a DIC microscope, in accordance with one or more embodiments of the invention.

FIG. 5 illustrates another configuration of a DIC microscope 300 in accordance with one or more embodiments of the invention. As illustrated, an optical system (i.e., lens 502) is used to project the specimen 304 onto the plane of the two interference apertures 306 and 308. The phase difference information of the specimen 304 can be decoded by the Young's interference 310 pattern on the CCD sensor 312. The image of the specimen 304 can either be scanned across the interference apertures 306 and 308 or scan the interference apertures 306 and 308 across the image of the specimen 304 to get all of the information of differential phase contrast from the whole specimen 304.

Figure 6:
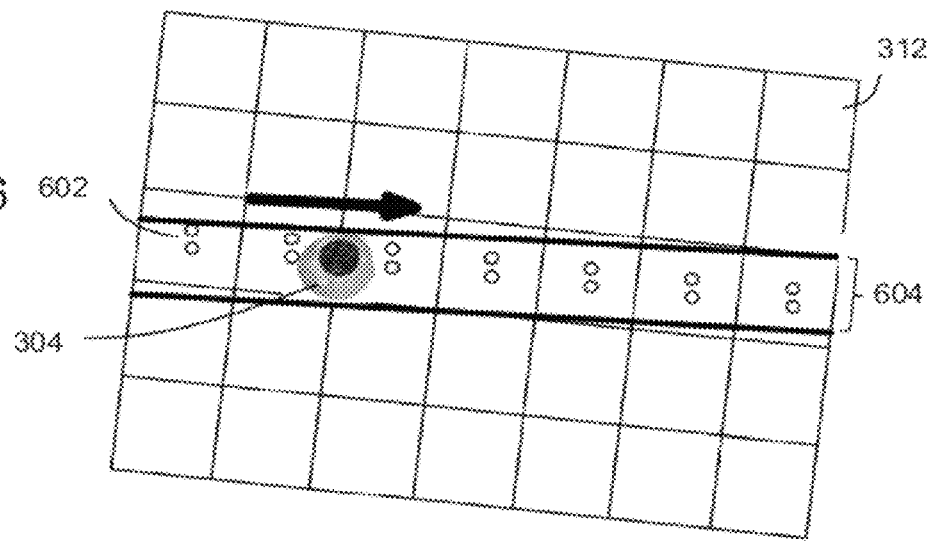
FIG. 6 is a schematic drawing of an on-chip DIC imaging system using the optofluidic microscope (OFM) technique, in accordance with one or more embodiments of the invention.

In addition to the above, an optofluidic microscope (OFM) technique can be combined with the DIC microscope 300 to implement an on-chip DIC imaging as illustrated in FIG. 6. An example of an optofluidic microscope (OFM) can be found in Cui, X., Heng, X., Erickson, D., Psaltis, D., Yang, C. "Portable optical microscope-on-a-chip" Photonics West, San Jose, Calif., January 2006, which is hereby incorporated by reference in its entirety for all purposes. In FIG. 6, the DIC-OFM device includes a plurality of apertures 602 in the form of a two parallel single-dimensional arrays of aperture structures. In this case, the aperture structures are aperture pairs. A gap may be located between the aperture layer and the light detector receiving light passing through the apertures. The specimen 304 passes through the fluid channel 604 across the apertures 602. Each DIC microscope 300 can generate a line scan from the signal received from the light detector as the specimen 304 flows across the aperture array through the fluid channel 604. The image can be reconstructed from the line scans.

As illustrated in FIG. 6, the light detector 312 may include a plurality of light detecting elements (e.g., sensor pixels). In this example, the plurality of light detecting elements is in the form of a two dimensional array. In one or more embodiments, a single light detecting element (e.g., sensor pixel) is associated with an aperture pair 602 in the center of each sensor pixel. Further, the fluid channel 604 is oriented at an angle with respect to the pixels. Accordingly, each aperture pair 602 is centered over a light detecting element while the fluid channel 604 is angled over the light detecting elements. Such an arrangement, provides the ability to better determine DIC information about the specimen 304 (e.g., via analysis of the light intensity distribution 314) while the specimen 304 flows across the channel 604.

Figure 3:
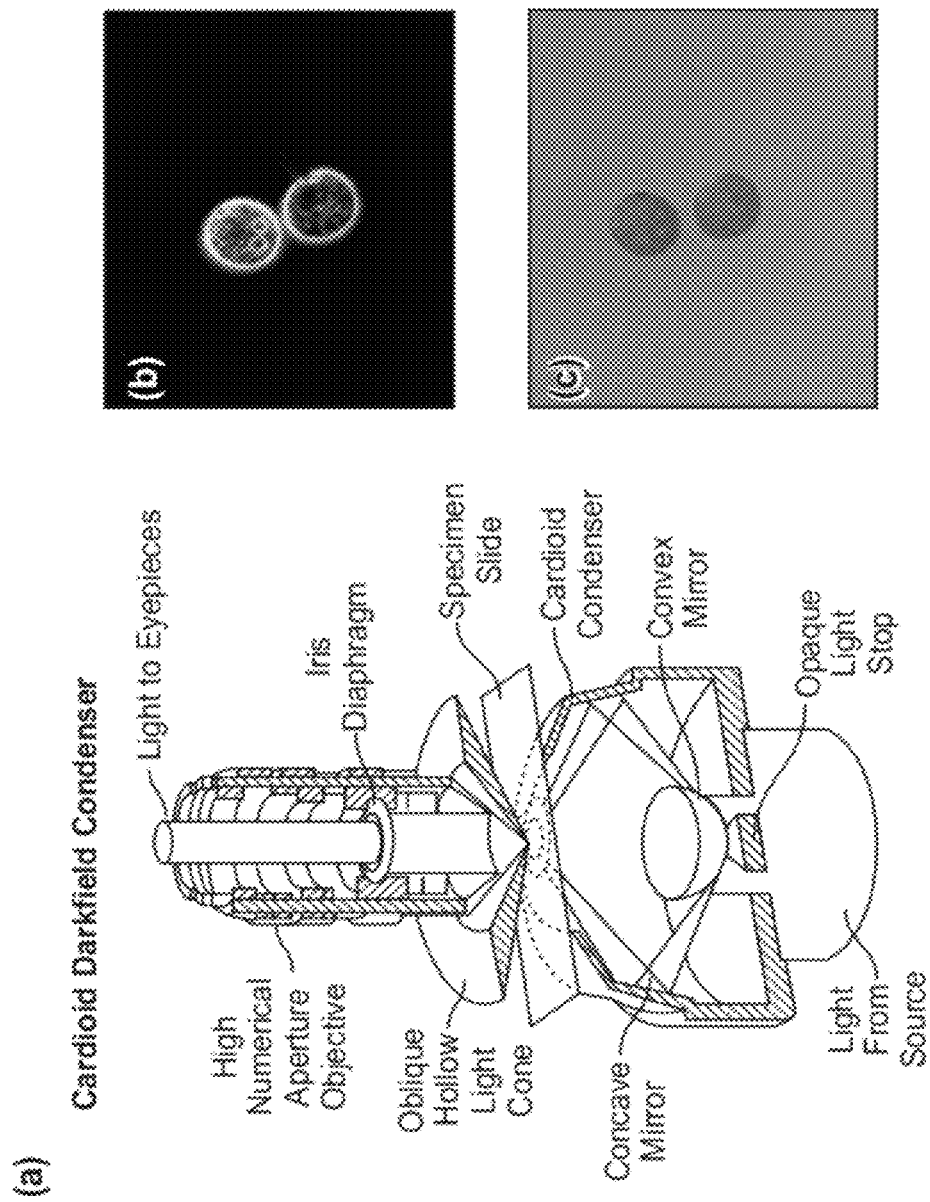
FIG. 3(a) is a schematic drawing of portions of a conventional darkfield microscope having a cardioid darkfield condenser.
FIG. 3(b) is a darkfield image of *Chlamydomonas* generated using the conventional darkfield microscope.
FIG. 3(c) is a bright field image of *Chlamydomonas* generated using a bright field microscope.
Figure 7:
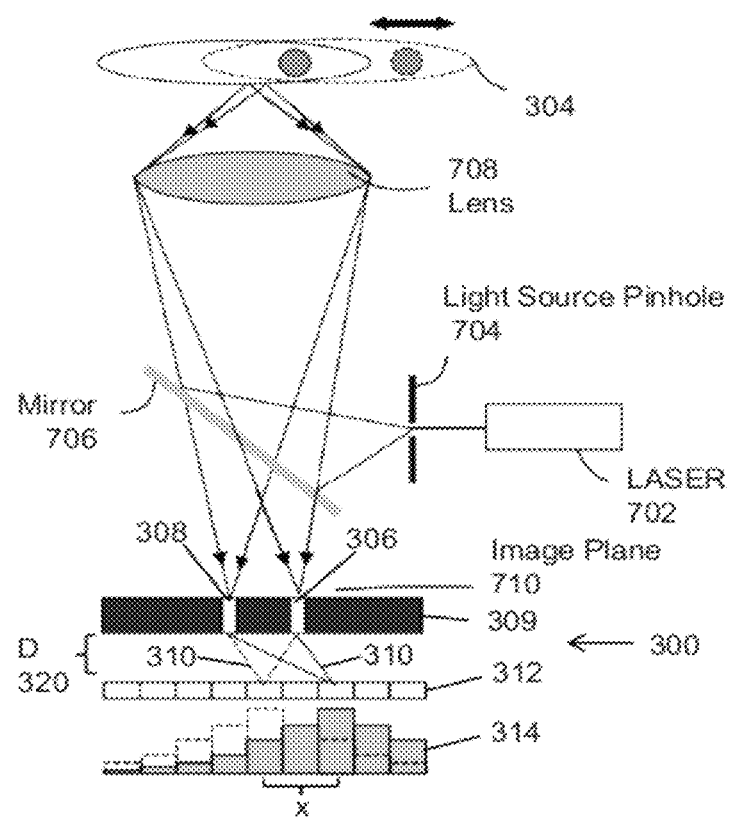
FIG. 7 is a schematic drawing of a confocal microscope technique combined with a DIC microscope to implement a confocal DIC imaging microscope, in accordance with one or more embodiments of the invention.

Embodiments of the invention may also combine the confocal microscope technique with the DIC microscope (described above) to implement a confocal DIC imaging microscope as illustrated in FIG. 7. An example of the confocal microscope technique can be found in Dunn, Wang, Paddock, Hzen, DeVries, Pawley, Parry-Hill, Fellers, and Davidson, "Introduction to Confocal Microscopy," 2007, available from MicroscopyU at http://www.microscopyu.com/articles/confocal/, which is hereby incorporated by reference in its entirety for all purposes. If the DIC microscope (e.g., item 300 of FIG. 3) is applied to the setup similar to a confocal microscope, the interference apertures 306-308 in the DIC microscope 300 can act as a spatial filter as the detector pinhole in confocal microscope.

The difference between the prior microscopes described herein and the confocal DIC imaging microscope of FIG. 7 is that there are two spatial filter pinholes (e.g., apertures 304, 306), which can grab information from two 3D localized spots in the specimen 304 simultaneously. The phase difference information between these two spots also can be decoded by the Young's interference pattern 310 on the light sensor 312. Accordingly, the 3D information of the differential phase contrast may be obtained from the specimen.

As illustrated in FIG. 7, the laser 702 passes through the light source pinhole 704 and is reflected by the mirror 706 and the lens 708 to illuminate the specimen 304. Accordingly, FIG. 7 illustrates a reflective mode microscope since the light that is used to illuminate the specimen plane 304 from the bottom while maintaining the image plane 710 immediately above the apertures 304, 306.

In the above descriptions, the light detector 312 may be described as a CCD sensor. However, a CMOS, a position sensitive device (PSD) or other kinds of photo detectors can be used.

Referring again to FIGS. 4A and 4B, it may be noted that the sensitivity of the differential phase detection in the DIC microscope (described herein) may be determined by the distance 318 between two interference apertures 304, 306, the distance 320 between the interference apertures 304, 306 and the photo detector 312, and the position sensitivity 316 of the photo detector. A spacer or a means/mechanism that provides the desired spacing 320 may be used. Further, the lateral resolution of the DIC microscope 300 may be determined by the distance 318 between the two apertures 304, 306. Proper care in the design should be taken to meet to the requirement of the specific application.

Potential applications of embodiments of the invention include inexpensive high resolution and more capable DIC imaging as well as on-chip DIC imaging devices. In addition, the measurement of phase may be used in various contexts such as an interferometer/DIC microscope or as a Wavefront sensor/Shack Hartmann device.

Using embodiments of the invention, a Gaussian laser beam or an optical vortex may also be profiled. The quantitative measurement of laser beam profiles may be useful for ensuring the efficient and accurate use of lasers in applications ranging from laser machining to fiber optics to laser eye surgery. In addition, precise knowledge of the focal field distribution of high-NA lenses may be important in the design of systems such as confocal laser scanning microscopy and optical serial sectioning microscopy.

Figure 8:
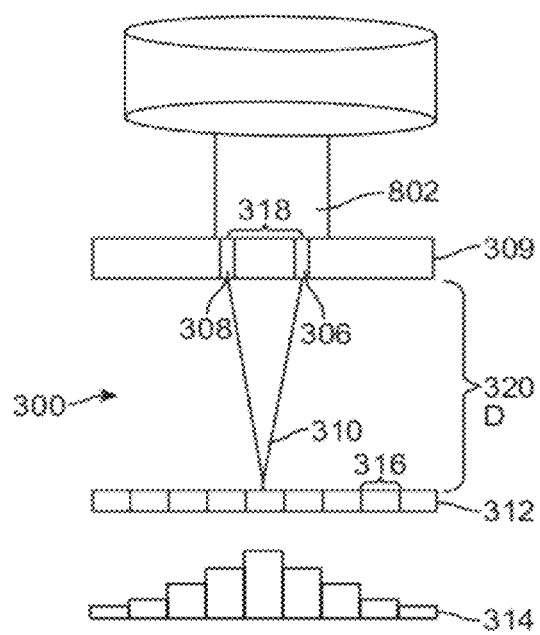
FIG. 8 is a schematic drawing of a single axis on-chip DIC phase beam profiler, in accordance with or more embodiments of the invention.
Figure 9:
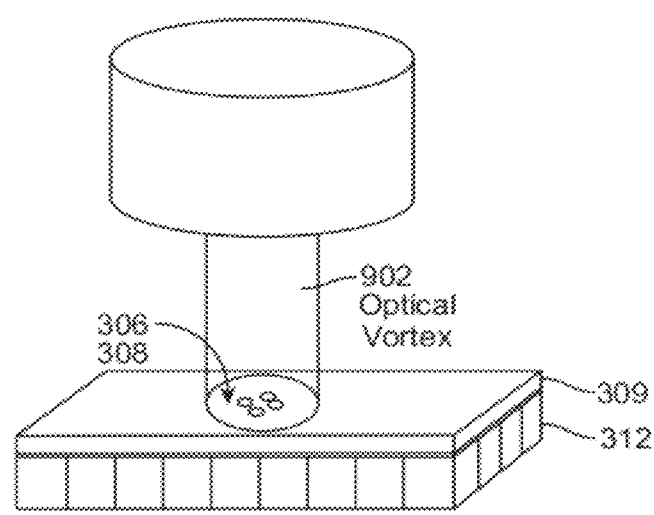
FIG. 9 is a schematic drawing of a dual axes DIC device, in accordance with one or more embodiments of the invention.

FIG. 8 illustrates a single axis on-chip DIC phase beam profiler in accordance with or more embodiments of the invention. Rather than illuminating a specimen as illustrated in FIG. 3-6, a single axis laser beam 802 may be projected onto the apertures 306-308. Four apertures 306-308 may also be used to create a dual axes on-chip DIC phase beam profiler in accordance with one or more embodiments of the invention. FIG. 9 illustrates a dual axis DIC that may be used in accordance with one or more embodiments of the invention. As illustrated the optical vortex 902 from the beam is shown through four apertures onto a light detector 312.

In addition to the above, a high-resolution portable beam profiler may be based on a slanted linear array of apertures, termed a slanted hole array beam profiler (SHArP). Apertures may be holes directly fabricated on sensor such as a metal-coated CMOS imaging sensor. With a single linear scan, the aperture array can establish a virtual grid of sampling points for beam profiling. The size of the apertures can be adjusted to increase/improve resolution. Such a methodology is further described in Xiquan Cui, Xin Heng, Jigang Wu, Zahid Yaqoob, Axel Scherer, Demetri Psaltis, and Changhuei Yang, "Slanted hole array beam profiler (SHArP)—a high-resolution portable beam profiler based on a linear aperture array," Optics Letters, Vol. 21, No. 21, Nov. 1, 2006, pp. 3161-3163, which is hereby incorporated by reference in its entirety for all purposes.

In addition, to the above, it may be noted that a DIC microscope may be qualitative and non-linear in nature. In this regard, a DIC image may be a mix of amplitude and phase information. Accordingly, it may be useful to obtain the actual phase, instead of a directional phase gradient. Embodiments of the invention provide a non-iterative and robust phase reconstruction method. Such a method may apply a Fourier-space integration approach that is direct, straightforward and reasonably accurate for images that do not contain discontinuities (e.g., biological phase images). An example of a Fourier-space integration approach can be found in M. R. Arnison, K. G. Larkin, C. J. R. Sheppard, N. I. Smith, and C. J. Cogswell, "Linear phase imaging using differential interference contrast microscopy," Journal of Microscopy, Vol. 214, Part I, April 2004, pp. 7-12, which is hereby incorporated by reference in its entirety for all purposes.

Figure 10:
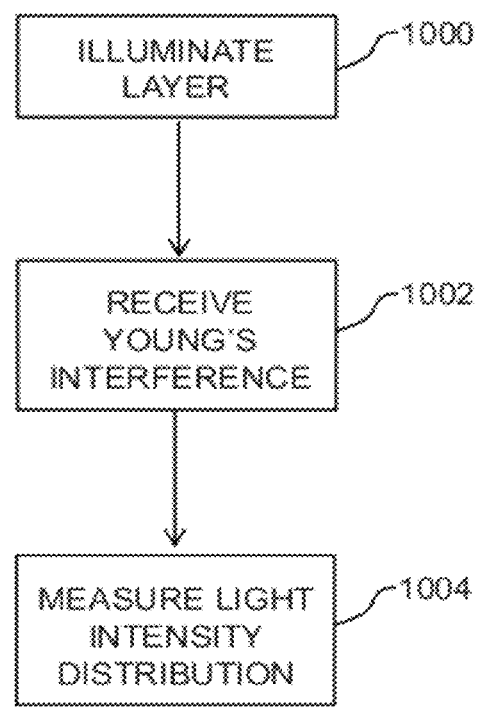
FIG. 10 is a flow chart illustrating a method for determining phase, in accordance with one or more embodiments of the invention.

FIG. 10 is a flow chart illustrating a method for determining phase in accordance with one or more embodiments of the invention. At step 1000, an aperture layer is illuminated. The aperture layer comprises a plurality of apertures. In a microscope embodiment, a specimen may be placed between the illumination source and the aperture layer. Further, the specimen may move across the apertures in the aperture layer (or the microscope can be moved across the specimen). Alternatively, a lens may be used to project the specimen onto a plane of the apertures. In an alternate embodiment (i.e., a beam profiling device), the aperture layer may be illuminated by a laser beam.

At step 1002, the light detector receives the light showing Young's interference, through the apertures.

At step 1004, the light intensity distribution is measured by the light detector. As described above, a specimen may be placed between the illuminating source and the layer and a differential phase contrast of the specimen is determined by the light intensity distribution (i.e., received/measured by the light detector). In a phase beam profiling embodiment, a beam profile of the laser beam is determined based on the light intensity distribution measured by the light detector. It should be noted that a similar embodiments and method may be utilized to produce a light field profiler in accordance with one or more embodiments of the invention.

Alternatively, in an optofluidic DIC microscope embodiment, the specimen may be passed through a fluid channel of a body. In some cases, a surface layer of the fluid channel may be the aperture layer having a plurality of apertures. The apertures may be in the form of an array of groups of light transmissive regions of at least two apertures. The light detector may comprises a two-dimensional (2D) array of light detecting elements with a single corresponding element of the 2D array configured to receive Young's interference from each of the groups of apertures. To create Young's interference, a gap exists between the aperture layer and the light detector. The specimen flows in the fluid channel across the multiple aperture structures and each corresponding light detecting element of the 2D array receives a line scan of the specimen.

In addition to the above, in either phase-beam profiling embodiment or a DIC microscope embodiment, the device may be fabricated/implemented in an on-chip device.

II. Surface Wave Assisted Optofluidic Microscope/Light Field Profiler

Signal transmission can be enhanced and suppressed in devices using an aperture layer with corrugations of grooves around the apertures. Embodiments of the invention use corrugation in the aperture layer in different patterns. These embodiments are described below, in section IV, and in other sections.

A. Dark Field OFM and Improvement of the Detection Sensitivity

Optical transmission through an aperture or other light transmissive region on a periodically corrugated surface has been examined in the prior art. Both transmission enhancement and suppression have been observed in Lezec, H. J., et al., "Beaming light from a subwavelength aperture," Science, 2002, 297 (5582), p. 820-822, Ebbesen, T. W., et al., "Extraordinary optical transmission through sub-wavelength hole arrays, Nature," 1998. 391(6668): p. 667-669 and D. Pacifici, et al., "Quantitative determination of optical transmission through subwavelength slit arrays in Ag films: Role of surface wave interference and local coupling between adjacent slits," *Physical Review B*, vol. 77, p. 115411, 2008, which are hereby incorporated by reference in their entirety for all purposes. Henri Lezec and his colleagues used a new model called composite diffracted evanescent waves (CDEWs) to explain the unexpected transmission suppression in Lezec, H. J. and T. Thio, "Diffracted evanescent wave model for enhanced and suppressed optical transmission through sub-wavelength hole arrays," Optics Express, 2004, 12 (16), p. 3629-3651, which is hereby incorporated by reference in its entirety for all purposes.

Such phenomenon may also be explained by surface waves. The suppression of the optical transmission through an aperture occurs when there is destructive interference between the optical wave coming through the aperture and the optical wave that is channeled in from the peripheral surface waves. A surface wave comprises a surface Plasmon component, a surface scattered component, or other suitable surface wave components, or any suitable combination thereof. In many embodiments, a surface wave consists of a surface Plasmon component and a surface scattered component. A surface Plasmon wave refers to the electromagnetic surface wave existing at the interface between a dielectric and a noble metal. An example of a surface Plasmon wave can be found in S. Maier, "Plasmonics: fundamentals and applications," Springer Verlag, 2007, which is hereby incorporated by reference in its entirety for all purposes. An example of evidence of a surface scaterred wave can be found in H. Lezec and T. Thio, "Diffracted evanescent wave model for enhanced and suppressed optical transmission through subwavelength hole arrays," Optics express, vol. 12, pp. 3629-3651, 2004, L. Chen, et al., "Role of radiation and surface plasmon polaritons in the optical interactions between a nano-slit and a nano-groove on a metal surface," Optics Express, vol. 14, pp. 12629-12636, 2006, G. Gay, et al., "The optical response of nanostructured surfaces and the composite diffracted evanescent wave model," Nat Phys, vol. 2, pp. 262-267, 2006, P. Lalanne and J. Hugonin, "Interaction between optical nano-objects at metallo-dielectric interfaces," Nature Physics, vol. 2, p. 551, 2006, L. Aigouy, et al., "Near-field analysis of surface waves launched at nanoslit apertures," Physical Review Letters, vol. 98, p. 153902, 2007, H. Liu and P. Lalanne, "Microscopic theory of the extraordinary optical transmission," Nature, vol. 452, pp. 728-731, 2008, and B. Ung and Y. Sheng, "Optical surface waves over metallo-dielectric nanostructures: Sommerfeld integrals revisited," Optics Express, vol. 16, pp. 9073-9086, 2008, which are hereby incorporated by reference in their entirety for all purposes.

Figure 11:
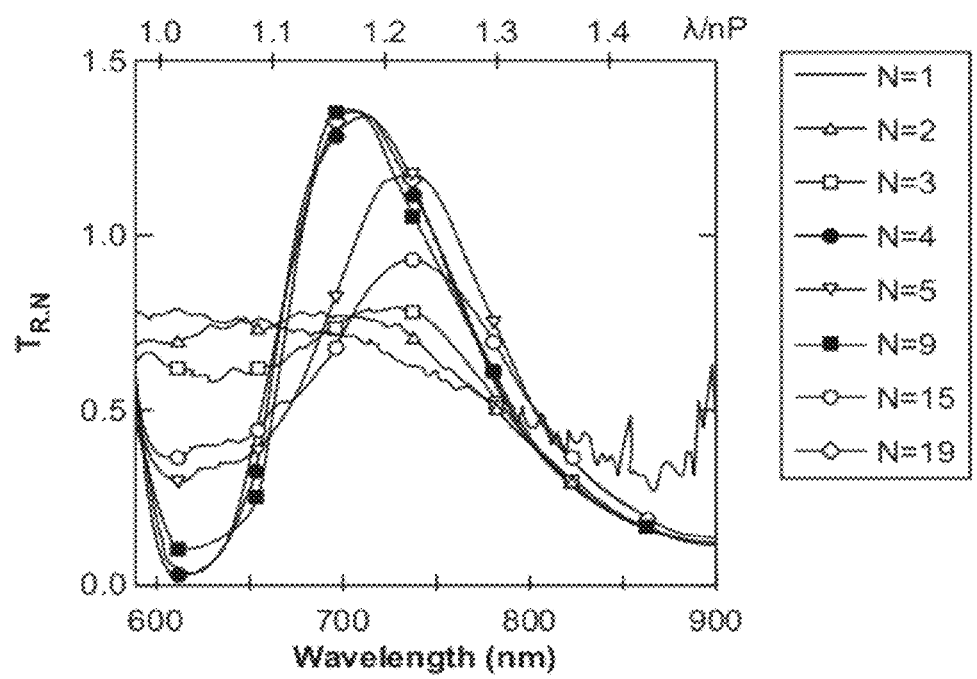
FIG. 11 is a graph of an abnormal transmission of a square aperture array for visible and near-IR light, in accordance with one or more embodiments of the invention.

FIG. 11 illustrates an abnormal transmission of a square aperture array (physically similar to one aperture on a corrugated surface) for visible and near-IR light. The value of N corresponds to the number of apertures in a row and a column. The phenomenon of the transmission suppression can be used in one or more embodiments of the invention based on an optofluidic microscope (OFM) setup and can help improve the optical detection.

Figure 12:
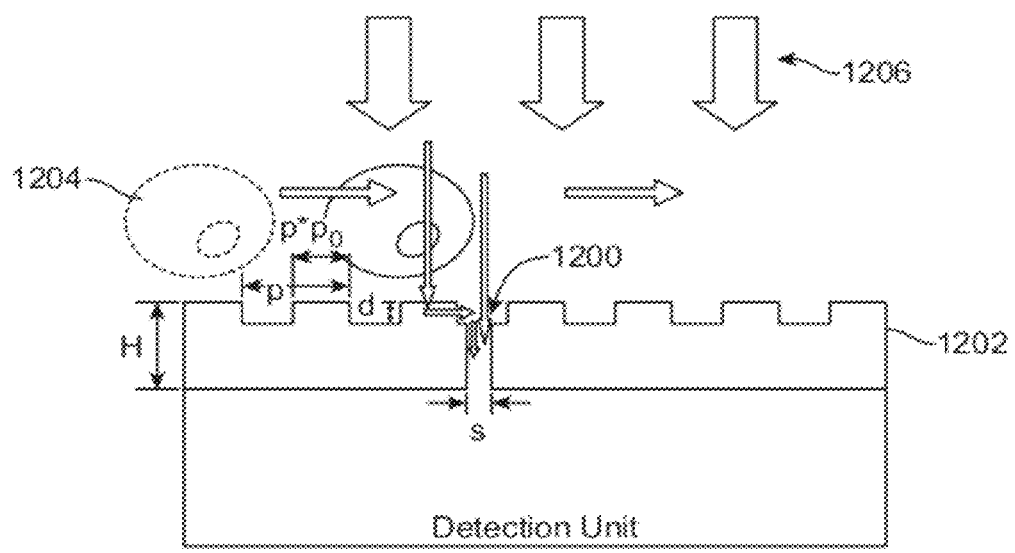
FIG. 12 is a schematic drawing of a corrugated surface an aperture on a layer configured, in accordance with one or more embodiments of the invention.

FIG. 12 illustrates an aperture 1200 with diameter d etched through a corrugated surface 1202 (periodicity "p," duty cycle "$p_0$," depth "d", thickness "H"). As illustrated, the aperture 1200 of size s (e.g., diameter) is used as an imaging probe while the specimen 1204 passes through the fluid channel having the corrugated surface 1202. The corrugated surface 1202 can be made in an opaque silver or aluminum film by using electron beam lithography or focused ion beam (FIB). A continuous wave (cw) laser at single wavelength at normal incidence provides the illumination 1206.

The transmission of the aperture 1200 on the corrugated surface 1202 in the visible band and IR band was studied by Lezec et al in Lezec, H. J., et al., "Beaming light from a subwavelength aperture," Science, 2002. 297 (5582), p. 820-822. At a specific wavelength ($\lambda_0$), optical transmission is at minima and is apparently weaker than that of an isolated aperture (as can be seen in FIG. 11). In the context of OFM, when there is no sample 1204 present, the detector receives a minimum amount of photons and only gives a weak dark field signal.

When a sample 1204 passes over the aperture 1200 array by use of microfluidic driven flow, it will introduce changes in the amplitude and phase of both the optical wave directly through the aperture 1200 and the surface wave on its peripheral. The condition of destructive interference no longer holds, and the transmission increases from the minimum value which indicates the presence of a sample 1204. This detection scheme is similar to dark field optical microscopy where the illumination background is originally dark and the introduction of optical discontinuity of the sample 1204 makes it look bright on a dark background. This technique has a signal to noise sensitivity advantage over bright field geometry.

In accordance with one or more embodiments of the invention, a spherical cell 1204 may be used to explain the operations of dark-field OFM. In FIG. 12, a laser source provides a uniform illumination 1206 on the plane of the aperture 1200 region. The parameters of the corrugated surface 1202 are selected such that the transmission of the aperture 1200 is suppressed. As was described above, such suppression is caused by the destructive interference between optical wave transmitted directly through the aperture 1200 and the peripheral surface waves. Therefore, the signal detected by the detection unit underneath the layer/corrugated surface 1202 will be weak. The detection unit can be a CMOS sensor directly attached to the layer 1202 or a microscope relay system that maps the transmission of the aperture 1200 onto a linear sensor array.

Now, consider the situation where a cell 1204 passes over the aperture 1200 by an appropriate microflow driving scheme, such as electrokinetics, pressure gradient or dielectrophoresis. When the cell 1204 is far away from the aperture 1200, the cell 1204 has negligible impact on changing the destructive interference condition between the optical wave and the surface wave. Thus, the detector's signal remains weak. However, when the cell 1204 arrives at the aperture 1200, the cell 1204 will change the intrinsic phase of one or both of the two electromagnetic waves. This change is due to the slight optical property discontinuity (e.g. refractive index, absorption coefficient) between the cell 1204 and the medium within which it is suspended. Note that the discontinuity in optical property between cell 1204 and the medium may be subtle and may have little effect in bright field microscope. However, in dark-field OFM, the accumulated phase shift disrupts the original condition of destructive inference, and thus the optical transmission signal will become much stronger, which will be readily registered by the detector as a signal change.

Various schemes may be used to implement one or more embodiments of the invention using dark field microscopy. The goal of such schemes is to create a corrugated surface/grating factor Gm having a defined period (e.g., via an etching and/or fabrication process) such that the surface wave polariton $\overrightarrow{K_{spp}}$ is equal to the optical wave on the surface (parallel) $K_{parallel}$:

$$\overrightarrow{K_{spp}} = \overrightarrow{K_{parallel}} + \overrightarrow{G_m}$$

A constant value $\overrightarrow{\beta}$ may also be added to further enhance the resolution and transmission:

$$\overrightarrow{K_{spp}} = \overrightarrow{K_{parallel}} + \overrightarrow{G_m} + \overrightarrow{\beta}$$

In accordance with the above equations, various schemas may be utilized to optimize the transmission and resolution received via an aperture. Schemas 1-4 below utilize a periodic corrugation on the top surface of the aperture layer (e.g., a metallic film) in an optofluidic microscope. Schema 5 illustrates the use of a periodic corrugation on both the top and bottom surface.

It should also be noted that the principles described herein may be utilized in a light field profiler.

Scheme 1

Figure 13:
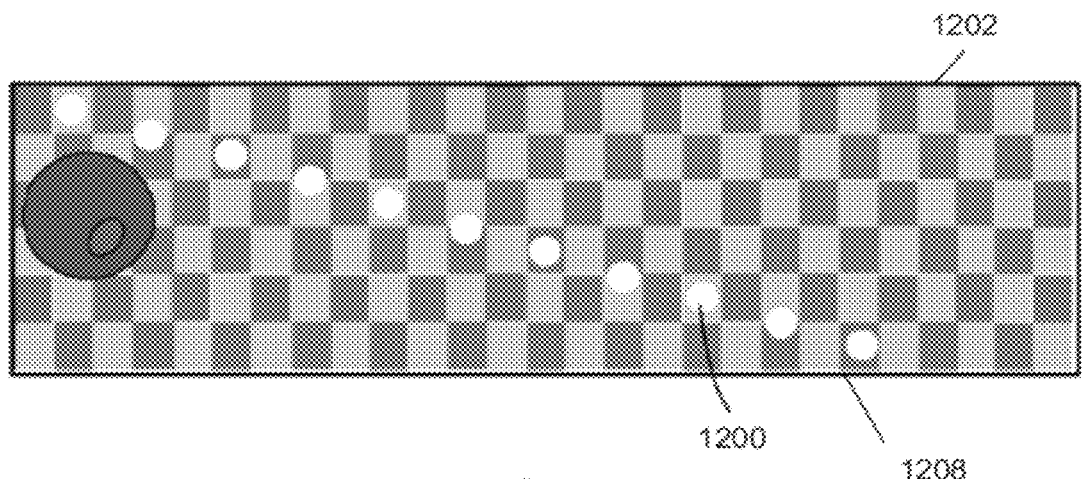
FIG. 13 is a schematic drawing illustrating a scheme wherein grey colors schematize surface corrugation that will appear different under a microscope, in accordance with one or more embodiments of the invention.

FIG. 13 illustrates a scheme wherein grey colors schematize surface corrugation that will appear different under a microscope. As illustrated, the apertures 1200 are laid down in a slanted fashion on a background of a corrugation surface 1202 (duty cycle of dimples chosen as 50%) with a rectangular lattice 1208. One advantage associated with such a rectangular lattice is that its fabrication on a relatively large area is simple. As the aperture 1200 sizes are the same, the same "superlattice" structure will work for all of apertures 1200 because the apertures 1200 share the same momentum conservation considerations. Such a mesh checkerboard pattern type of corrugation has been shown to enhance the transmission via the apertures 1200.

Scheme 2

Figure 14:
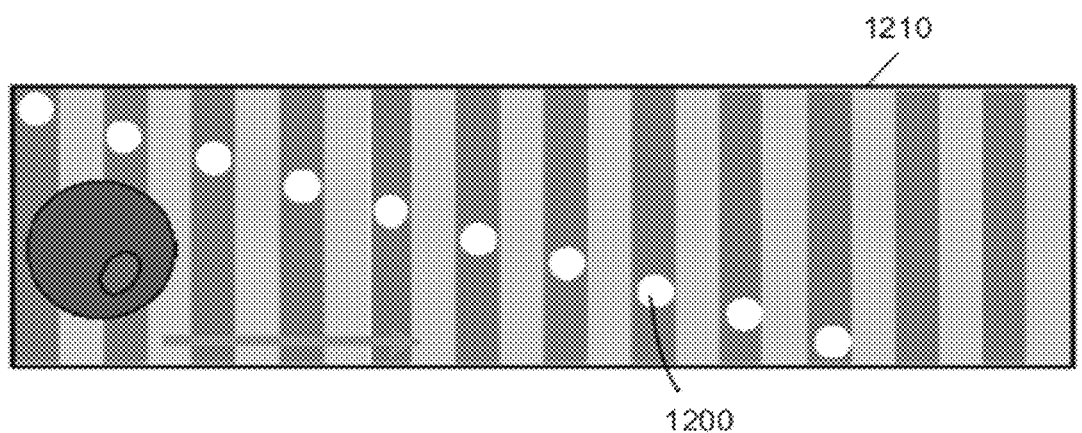
FIG. 14 is a schematic drawing illustrating a schema wherein a two dimensional rectangular lattice-structure (i.e., of FIG. 13) is replaced with a 1D grating structure, in accordance with one or more embodiments of the invention.

FIG. 14 illustrates a schema wherein the two dimensional rectangular lattice-structure 1208 (i.e., of FIG. 13) is replaced with a 1D grating structure 12010. No matter whether surface plasmon waves or surface composite diffracted evanescent waves (CDEWs) are applied to explain optical transmission suppression of the aperture, destructive interference conditions can be satisfied by using 1D grating 1210 and 1D surface waves, as long as the incidence wave does not contain a wave vector component perpendicular to the micro-flow direction. Again, the use of such a 1D grating structure 1210 having a defined period serves to enhance the transmission received through apertures 1200 while providing increased resolution.

Scheme 3

Figure 15:
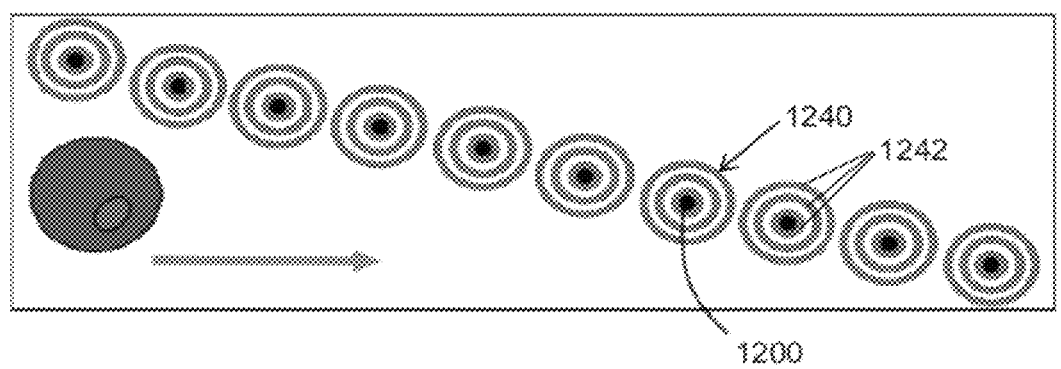
FIG. 15 is a schematic drawing illustrating the use of a corrugated ring structure, in accordance with one or more embodiments of the invention.

It has been shown that the anomalous transmission phenomenon can also be observed in a ring structure with a through-hole at the center of the concentric rings in Lezec, H. J., et al., "Beaming light from a subwavelength aperture," Science, 2002, 297 (5582), p. 820-822. Such a configuration may also be used in dark-field OFM and the physics behind the destructive interference is similar to the two previous cases. This publication is hereby incorporated by reference in its entirety for all purposes. FIG. 15 illustrates the use of such a ring structure 1240 in accordance with one or more embodiments of the invention. Thus, as illustrated in FIG. 15, concentric circle corrugations 1242 are used to enhance the transmission through apertures 1200.

Scheme 4

Knowledge of the length of nano-particles can be an invaluable resource. For example, numerous applications of microfluidics based nano-rulers have been useful in biological research, such as measuring the length of the extended DNA molecules and the distance between two fluorescent cells within a microorganism. An example of measuring the length of the extended DNA molecules can be found in Tegenfeldt, J. O., et al., "Near-field scanner for moving molecules," Physical review letters, 2001, 86 (7), pp. 1378-1381 and Tegenfeldt, J. O., et al., "Micro- and nanofluidics for DNA analysis, Analytical and Bioanalytical Chemistry," 2004, 378 (7), pp. 1678-1692, which are hereby incorporated by reference in their entirety for all purposes.

Figure 16:
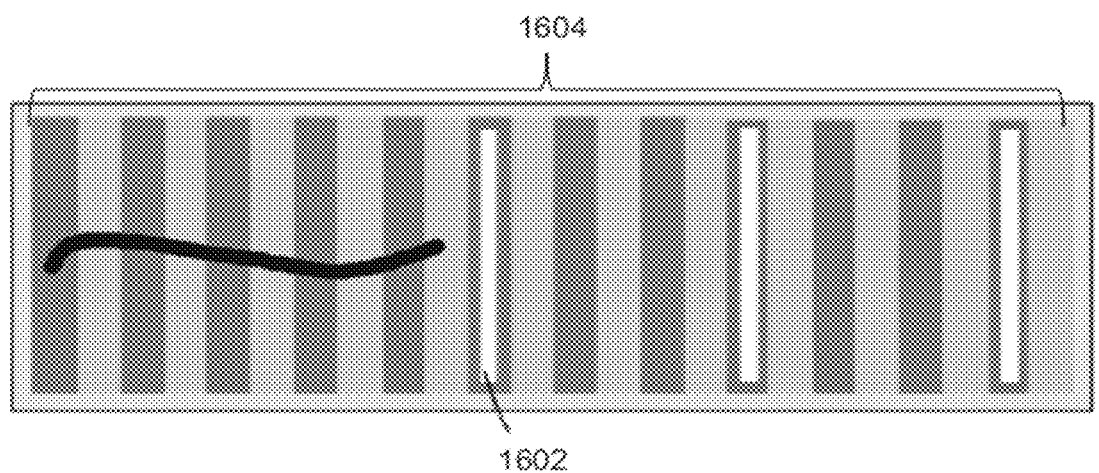
FIG. 16 is a schematic drawing of the use of a microfluidic based nano-ruler, in accordance with one or more embodiments of the invention.

Dark-field OFM can be readily modified for this type of application. It can be applied as a high-resolution ruler or particle sorter in microfluidic settings. FIG. 16 illustrates the use of a microfluidic based nano-ruler in accordance with one or more embodiments of the invention. As illustrated, the size of the slit 1602 can affect the resolution similar to the size of an aperture 1200. In this regard, the smaller the slit or aperture, the higher the resolution. However, as the size of the slit 1200 decreases, the transmission quality decreases. Accordingly, what is needed is the capability to maintain a high resolution (i.e., via a small slit 1602) while enhancing the transmission. A corrugation pattern 1604 such as that illustrated in FIG. 16 serves to enhance the transmission in a desirable manner. In FIG. 16, a corrugation pattern 1604 similar to that used in schema 2 (i.e., FIG. 14) is used.

Scheme 5

Figure 17:
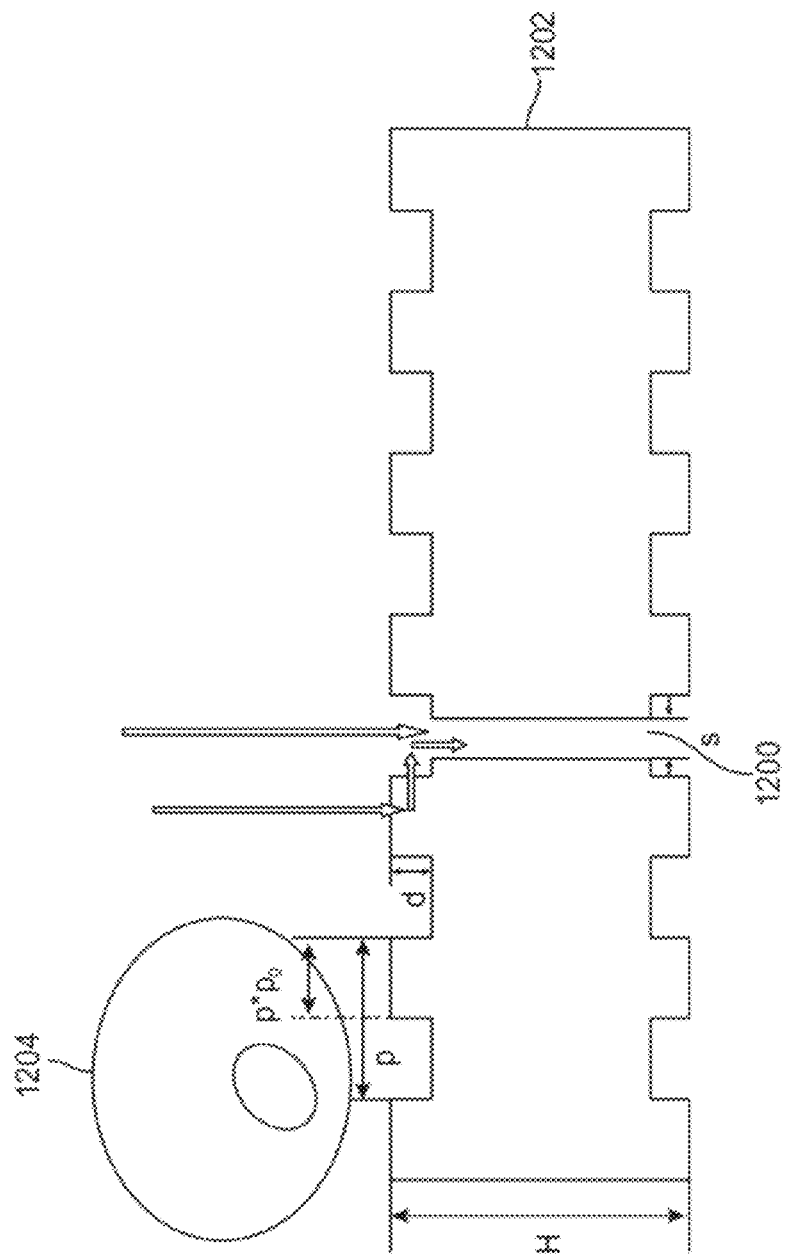
FIG. 17 is a schematic drawing of a periodical configuration fabricated on the top and bottom of a surface containing apertures, in accordance with one or more embodiments of the invention.

In order to facilitate the coupling between surface waves at the top surface and the bottom surface, periodical corrugation can be made on both the bottom and top surfaces as shown in FIG. 17. The parameters used in the design, e.g. d (depth of corrugation), p (period), s (size of aperture), H (height of the aperture layer) and $p_0$ (duty cycle) denote the same features as those in FIG. 12. Making surface corrugation on the bottom surface results in a more directed transmitted light beam can be shown in Lezec, H. J., et al., "Beaming light from a subwavelength aperture," Science, 2002, 297 (5582), pp. 820-822. This beam can be much more efficiently collected by an objective lens or a CMOS sensor. The type of device may be made as a free-standing structure, and the fabrication procedure has been demonstrated in Lezec, H. J., et al., "Beaming light from a subwavelength aperture," Science, 2002. 297 (5582), pp. 820-822.

III. Bright Field OFM and Enhancement of Optical Transmission Through a Subwavelength Aperture The surface waves are considered as collective electron excitations, which are characterized by intensive electromagnetic fields confined on the surface of highly conductive metal (e.g. Al, Ag, Au). The interaction of surface waves with probe light is able to enhance the transmission through subwavelength apertures.

In the visible spectral range, the surface waves have a larger momentum (wave number) than propagating light, so the surface waves do not couple to each other efficiently without fine local structures, usually nanostructures. Careful selection of the parameters in FIGS. 12 and 17 can result in strong coupling between light and surface waves, which enhances the transmission through apertures. The well accepted momentum matching formula is:

$$K_{sp} = K_0 + mG_x + lG,$$

$K_{sp}$ is the wave vector of a surface wave $$K_{sp}(\omega) = \frac{\omega}{c}\sqrt{\frac{\varepsilon_m(\omega)\varepsilon_s}{\varepsilon_m(\omega)+\varepsilon_s}}, \varepsilon_s: \text{dielectric medium}, \varepsilon_m: \text{metal} \quad (2)$$

$K_0$ is the wave vector of light in the top dielectric medium.

$$G_x = \frac{2\pi}{L_x}$$

is the 1st order vector in the x direction of the reciprocal lattice of the periodical corrugation.

$$G_y = \frac{2\pi}{L_y}$$

is the 1st order vector in the y direction of the reciprocal lattice of the periodical corrugation.

Note that the above formulas are only approximations for satisfying the surface wave-light resonance condition; the dispersion relation of $K_{sp}$ is modified when the periodical surface corrugation is introduced. However this momentum matching formula works successfully when the corrugation is sufficiently shallow so that the impact on smooth-surface $K_{sp}$ is weak.

Under normal conditions, this light transmission is extremely weak and requires the use of photomultiplier tube (PMT) or avalanche photodiode (APD) detectors for detection. In other words, it precludes the use of a cheap optical detector such as a complimentary metal-oxide-semiconductor (CMOS) sensor as a detector option. Bright field OFM assisted by surface waves aims at making use of the enhancement in optical transmission through apertures (e.g. 100 nm in diameter) to significantly boost a weak transmission, and thereby enable the use of CMOS sensors.

The configurations of bright-field OFM are similar to those of dark-field OFM (see FIGS. 12-17), with only changes in the selection of design parameters (e.g. p, L, d, s, etc.). The resonance condition of surface wave-light coupling is very sensitive to the surrounding medium. Accordingly, the existence of a biological sample breaks down the resonance condition and will immediately change the transmission though the aperture.

Bright field OFM assisted by surface waves is considered very important for high resolution fluorescence imaging. Fluorescence signals carry rich and important biological information. Unfortunately, fluorescence is usually weak and efficient detection is accomplished by using a bulky detector, such as an APD or a PMT with a long integration time. With the surface wave light coupling condition tuned for a specific fluorescence band, the fluorescence signal will be able to efficiently couple into the aperture and be transmitted with an enhanced power.

In accordance with one or more embodiments of the invention, the interaction between surface waves and probing light is facilitated by the introduction of surface corrugations. The interference can be fined tuned for destructive interference condition in dark-field OFM as well as for constructive interference condition in bright field OFM.

Consider the case where an isolated aperture is drilled on a smooth metal surface. The propagation wave scattered by the sample when reaching a subwavelength aperture may not be transmitted efficiently. Only the near field component of the scattered light can efficiently couple with the surface wave. Careful design of structures surrounding the aperture not only enhances the interaction between the surface wave and the scattered light, but also facilitates the coupling of the surface wave to the underneath detector. In other words, the localized (near field) information of the sample can be more effectively coupled by the detector underneath the aperture.

The resolution of the aperture based optical imaging may be compromised to some extent due to the surface wave light coupling. This coupling is quite different from the case where an isolated aperture is used in OFM. Light beaming effect (its physics is approximately explained by equation 1 above) provides a better selection of the direction of probing light in both the far field and near field.

In addition, it may be noted that the interference between the surface wave and the directly transmitted wave can also be arranged to be at other relative phases. In the situation where the two waves are arranged to be 180 degrees out of phase, any change in the relative phase of the two waves will be maximally translated into transmission signal change.

Figure 18:
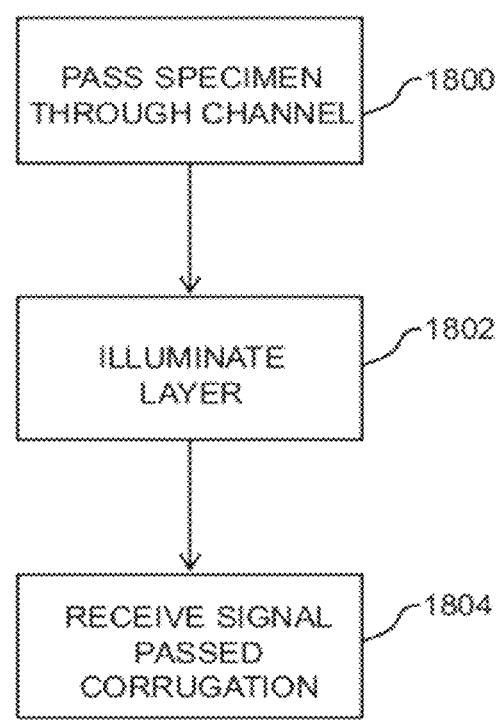
FIG. 18 is a flow chart illustrating a method of enhancing a transmission signal in a surface wave assisted optofluidic microscope, in accordance with one or more embodiments of the invention.

FIG. 18 is a flow chart illustrating the logical flow for enhancing a transmission signal in a surface wave assisted optofluidic microscope in accordance with one or more embodiments of the invention. At step 1800, a specimen is passed through a body comprising a fluid channel having a layer as a surface.

At step 1802, the layer is illuminated. As described above, the layer has at least one aperture that is configured to receive the illumination from an illumination source. Further, a surface wave propagates along the surface. The surface layer can be a metallic film in some cases.

At step 1804, a signal that is based on the illumination passing through the aperture is received on a light detector. In addition, a corrugation is fabricated onto the surface and parameters of the corrugation optimize the signal received on the light detector. Thus, the signal that is received passes across the corrugation thereby enhancing the transmission while maintaining a high resolution. Since the signal is based on the corrugation parameters, such parameters may be tuned to enhance destructive interference in a dark field microscope or may be tuned to enhance constructive interference in a bright field microscope.

The corrugation/corrugation parameters (e.g., grating) may be fabricated in accordance with various different schema. In one schema, multiple apertures are established in a slanted pattern on the corrugation having a rectangular lattice pattern. In a second schema, multiple apertures are established in slanted pattern on the corrugation having a 1D grating structure pattern. In a third schema, a slanted pattern of multiple apertures are established each in a center of the corrugation defined by concentric rings. In fourth schema, the length of a nanoparticle may be measured based on the signal received on the light detector (i.e., the corrugation and apertures/slits provide a nanoruler structure). In a fifth schema, the corrugation is fabricated onto both a top and bottom of the surface containing the apertures.

The different schemas described herein may be used in combination with the DIC microscopes and phase-beam profilers described above. In this regard, the layer used in the DIC microscopes may also have corrugated surfaces that provide a surface wave-assisted optofluidic microscope.

IV. SWEDA (Surface-Wave-Enabled Darkfield Aperture)

A. Darkfield Imaging

As discussed above, the ability of an optical sensor to detect light signals, especially weak light signals, can be limited by the presence of background light. As such, pre-detection background light suppression providing a darkfield can be important in image enhancement. Prior darkfield imaging devices such as conventional darkfield microscopes use complex and expensive components to generate a darkfield image. In addition, conventional darkfield imaging devices can be difficult to operate and require operator training.

B. The SWEDA Structure

In certain embodiments, one or more simple SWEDA structures can be used to generate a darkfield for sensing and imaging purposes. A simple SWEDA structure includes a metal layer with at least one surface having grooves around a darkfield aperture (SWEDA). The SWEDA structure operates by cancelling background light before it is transmitted through the darkfield aperture to a light sensor-predetection background cancellation. To function in this way, the features of the SWEDA structure are designed to induce a surface wave that balances and cancels out the direct transmission of light of a uniform light field from an illumination source. When the uniform field is disrupted by, for example, the presence of an object in the field, the balance is upset and light passes through the darkfield aperture. By implementing one or more SWEDA structures onto a light detector, the apertures receiving the uniform light transmit little or no light to the light detector and thereby create a darkfield for the light detector. A sensing device equipped with darkfield apertures can intrinsically cancel background light prior to signal detection, accomplishing darkfield sensing for a coherent light field in a robust, compact, and simple format.

Since the exact balance between the surface wave and direct transmission components is highly delicate and can be easily disrupted by the non-uniformity of the localized light field or light field deviation from normal incidence, the SWEDA structure can be used to suppress background light and allow for darkfield sensing and imaging. In some cases, a SWEDA structure can provide an image contrast enhancement of 27 dB. A detection system that can effectively suppress background light contributions (prior to detection) and allow detection of small signals in extremely compact device architectures can be advantageous for a broad range of applications from on-chip bio-sensing to metrology and microscopy.

In many embodiments, the design features of the SWEDA structure can be optimized to cancel out the direct transmission of light under a uniform light field. In some embodiments, the features can also be optimized to enhance the direct transmission of light through the darkfield aperture under a non-uniform light field. This enhancement will create a higher contrast image. In yet other embodiments, the features of the SWEDA structure can be designed to be highly sensitive to polarized light so that the SWEDA structure can be use in a polarization sensor.

The underlying principle of certain embodiments of the SWEDA structure is based on the light interaction between subwavelength features on a metal-dielectric interface. This interaction can be found in T. Ebbesen, et al., "Extraordinary optical transmission through sub-wavelength hole arrays," Nature, vol. 391, pp. 667-669, 1998, T. Thio, et al., "Enhanced light transmission through a single subwavelength aperture," Opt. Lett., vol. 26, pp. 1972-1974, 2001, H. Lezec, et al., "Beaming light from a subwavelength aperture," Science, vol. 297, pp. 820-822, 2002, T. Thio, et al., "Giant optical transmission of sub-wavelength apertures: physics and applications," Nanotechnology, vol. 13, pp. 429-432, 2002, H. Lezec and T. Thio, "Diffracted evanescent wave model for enhanced and suppressed optical transmission through subwavelength hole arrays," Optics express, vol. 12, pp. 3629-3651, 2004, R. Hollingsworth and R. Collins, "Plasmon enhanced near-field optical probes," ed: Google Patents, 2005, H. Schouten, et al., "Plasmon-assisted two-slit transmission: Young's experiment revisited," Physical Review Letters, vol. 94, p. 53901, 2005, L. Chen, et al., "Role of radiation and surface plasmon polaritons in the optical interactions between a nano-slit and a nano-groove on a metal surface," Optics Express, vol. 14, pp. 12629-12636, 2006, G. Gay, et al., "The optical response of nanostructured surfaces and the composite diffracted evanescent wave model," Nat Phys, vol. 2, pp. 262-267, 2006, P. Lalanne and J. Hugonin, "Interaction between optical nano-objects at metallo-dielectric interfaces," Nature Physics, vol. 2, p. 551, 2006, L. Aigouy, et al., "Near-field analysis of surface waves launched at nanoslit apertures," Physical Review Letters, vol. 98, p. 153902, 2007, D. Pacifici, et al., "All-optical modulation by plasmonic excitation of CdSe quantum dots," Nature photonics, vol. 1, pp. 402-406, 2007, A. Drezet, et al., "Miniature plasmonic wave plates," Physical Review Letters, vol. 101, p. 43902, 2008, E. Laux, et al., "Plasmonic photon sorters for spectral and polarimetric imaging," Nature Photonics, vol. 2, pp. 161-164, 2008, H. Liu and P. Lalanne, "Microscopic theory of the extraordinary optical transmission," Nature, vol. 452, pp. 728-731, 2008, D. Pacifici, et al., "Universal optical transmission features in periodic and quasiperiodic hole arrays," Optics Express, vol. 16, pp. 9222-9238, 2008, B. Ung and Y. Sheng, "Optical surface waves over metallo-dielectric nanostructures: Sommerfeld integrals revisited," Optics Express, vol. 16, pp. 9073-9086, 2008, and G. Gbur, et al., "Achieving superresolution in near-field optical data readout systems using surface plasmons," Applied Physics Letters, vol. 87, p. 191109, 2005, which are hereby incorporated by reference in their entirety for all purposes.

Surface waves are induced by the subwavelength features on the metal-dielectric interface. Examples of surface waves and their behavior can be found in S. Maier, "Plasmonics: fundamentals and application," Springer Verlag, 2007, Lezec and T. Thio, "Diffracted evanescent wave model for enhanced and suppressed optical transmission through subwavelength hole arrays," Optics express, vol. 12, pp. 3629-3651, 2004, L. Chen, et al., "Role of radiation and surface plasmon polaritons in the optical interactions between a nano-slit and a nano-groove on a metal surface," Optics Express, vol. 14, pp. 12629-12636, 2006, G. Gay, et al., "The optical response of nanostructured surfaces and the composite diffracted evanescent wave model," Nat Phys, vol. 2, pp. 262-267, 2006, P. Lalanne and J. Hugonin, "Interaction between optical nano-objects at metallo-dielectric interfaces," Nature Physics, vol.

2, p. 551, 2006, L. Aigouy, et al., "Near-field analysis of surface waves launched at nanoslit apertures," Physical Review Letters, vol. 98, p. 153902, 2007, H. Liu and P. Lalanne, "Microscopic theory of the extraordinary optical transmission," Nature, vol. 452, pp. 728-731, 2008, and B. Ung and Y. Sheng, "Optical surface waves over metallo-dielectric nanostructures: Sommerfeld integrals revisited," Optics Express, vol. 16, pp. 9073-9086, 2008, which are hereby incorporated by reference in their entirety for all purposes. Appropriately designed grooves around an aperture have been shown to change the total amount of light transmission through the aperture as shown in T. Thio, et al., "Enhanced light transmission through a single subwavelength aperture," Opt. Lett., vol. 26, pp. 1972-1974, 2001, T. Thio, et al., "Giant optical transmission of sub-wavelength apertures: physics and applications," Nanotechnology, vol. 13, pp. 429-432, 2002, H. Lezec and T. Thio, "Diffracted evanescent wave model for enhanced and suppressed optical transmission through subwavelength hole arrays," Optics express, vol. 12, pp. 3629-3651, 2004, G. Gay, et al., "The optical response of nanostructured surfaces and the composite diffracted evanescent wave model," Nat Phys, vol. 2, pp. 262-267, 2006, P. Lalanne and J. Hugonin, "Interaction between optical nano-objects at metallo-dielectric interfaces," Nature Physics, vol. 2, p. 551, 2006, D. Pacifici, et al., "All-optical modulation by plasmonic excitation of CdSe quantum dots," Nature photonics, vol. 1, pp. 402-406, 2007, and E. Laux, et al., "Plasmonic photon sorters for spectral and polarimetric imaging," Nature Photonics, vol. 2, pp. 161-164, 2008, which are hereby incorporated by reference in their entirety for all purposes.

The behavior of a groove-based SWEDA structure can be intuitively explained as follows. Surface waves are charge density waves that can be induced and sustained in certain types of materials (e.g, metals). Optical waves and surface waves have substantially different dispersion relationships. Yet, we can couple optical waves into surface waves and vice-versa by matching their energy and momentum using grooves in the SWEDA structure. This wave coupling on the SWEDA structure can be intuitively explained as follows. When light falls on the patterned groove pattern, it couples into a surface wave. By choosing a groove periodicity (i.e., distance between grooves) such that the surface wave launched at each groove adds up in phase, we can generate a strong propagative surface wave that is directed towards the SWEDA. The surface wave can then be converted back to a propagating optical wave at the central SWEDA. In essence, the groove structure serves as an antenna for light collection and uses the surface wave to transport the collected optical power to the SWEDA.

Embodiments of SWEDA structures provide one or more technical advantages. Generally, embodiments of SWEDA structures are advantageous because they provide a simple, compact, and relatively inexpensive design for effectively generating a darkfield. In one embodiment, a SWEDA structure has been shown to have a darkfield suppression factor of at least 1000. One advantage of embodiments is that the SWEDA structure is simple and compact, and easily adapted to being used on various sensing/imaging devices in a broad range of applications from on-chip bio-sensing to metrology and microscopy. For example, the SWEDA structure can be fabricated onto a sensor chip (e.g., CMOS sensor chip) which is easily implemented by plugging it into an imaging device (e.g., standard microscope). Another advantage of certain embodiments is that the SWEDA structure suppresses the background signal before detection by the sensor, so that a sensing/imaging device employing the SWEDA structure does not need an exotic and specialized condenser, or other expensive and bulky components to create a darkfield. Since the SWEDA structure alters the illumination light field, the collection optics of an imaging device employing the SWEDA structure can be unchanged. In addition, an operator using this imaging device employing the SWEDA structure (s) would not require extensive training on using the darkfield capabilities.

The SWEDA structure is comprised of an opaque or semi-opaque aperture layer has a darkfield aperture surrounded by a plurality of grooves. The plurality of grooves can be in any suitable pattern such as a circular groove pattern, a linear groove pattern, a rectangular groove pattern, an oval groove pattern, a checkerboard groove pattern, etc. Due to its circular symmetry nature, a SWEDA structure with grooves in a circular groove pattern can provide a polarization-independent behavior for signal detection and imaging. That is, a SWEDA structure having grooves in a circular groove pattern can suppress bright normal-incidence background regardless of the incident light field's polarization state. On the other hand, a SWEDA structure with grooves in a linear groove pattern can be highly sensitive to the polarization state of the incident light.

C. SWEDA Structure with a Circular Groove Pattern

Figure 19:
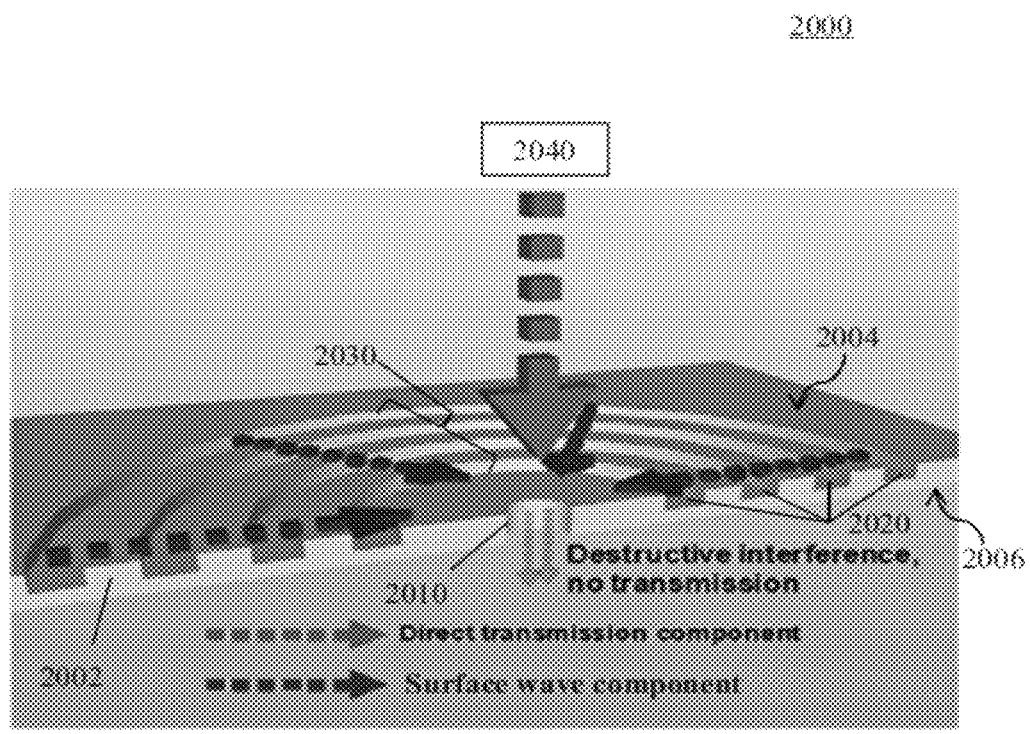
FIG. 19 is a schematic drawing of a SWEDA structure with a circular groove pattern, according to embodiments of the invention.

FIG. 19 is a schematic drawing of a SWEDA structure 2000 with a circular groove pattern, according to an embodiment of the invention. In this illustration, the SWEDA structure 2000 comprises an opaque or semi-opaque aperture layer 2002 having a first surface 2004 and a second surface 2006. The aperture layer 2002 has a darkfield aperture 2010 surrounded by a plurality of circular grooves 2020 forming a corrugation 2030 in the first surface 2004. An illumination source 2040 provides a uniform incident light field to the first surface 2004. In this illustration, the surface wave component destructively interferes with the direct transmission component cancelling it out so that no light is transmitted through the darkfield aperture 2010. Although the SWEDA structure 2000 of this example is shown to have grooves only on the first surface 2004, in other embodiments the SWEDA structure 2000 can have grooves 2020 on a second surface 2006, or on both first and second surfaces 2004, 2006. Due to the polarization-independent nature of the circular-groove based SWEDA, it can be used to suppress background light regardless of the polarization state of the incident light field.

An aperture layer 2002 can refer to a opaque or semi-opaque layer having at least a first surface 2004 and a second surface 2006, a darkfield aperture 2010, and one or more grooves 2020 around the darkfield apertures 2010 in one or more surfaces 2004, 2006. The aperture layer can be made of any suitable material such as gold, gold plated glass, etc. In one case, the aperture layer 2002 is a metallic layer. In another case, the aperture layer consists of a metallic layer over a transparent plate (e.g., a glass plate). The grooves 2020 can be in one or both of the first and second surfaces 2006. The aperture layer 2002 can have any suitable properties and dimensions (thickness, length, width). The thickness of the aperture layer 2002 can be any suitable thickness such as, for example, 30, 20 or 10 microns. In some cases, the type of material used in the aperture layer 2002 can affect roughness of the aperture layer 2002 and the sharpness of the features in the aperture layer 2002 which can affect the darkfield suppression factor.

As used herein, an aperture such as darkfield aperture 2010 refers to any suitable light transmissive region of any suitable size (e.g., 1 nm, 10 nm, 20 nm etc.) and any suitable cross sectional shape (e.g., circular, rectangular, oval, etc.). In many cases, an aperture is a hole. In some of these cases, the holes can be at least partially filled with a transparent material.

Although a single darkfield aperture 2010 is shown in many illustrated embodiments of the SWEDA structure 2000, other embodiments include multiple darkfield apertures in the aperture layer 2002. By using multiple darkfield apertures 2010, the amount of light transmitted through the apertures can be increased to increase light collection efficiency. In one embodiment, a SWEDA structure 2000 has multiple C-shape apertures to increase light collection efficiency. An example of a C-shaped aperture can be found in X. Shi, et al., "Ultra-high light transmission through a C-shaped nanoaperture," Optics letters, vol. 28, pp. 1320-1322, 2003, which is hereby incorporated by reference in its entirety for all purposes.

Grooves 2020 can refer to a furrow or channel in at least one surface of the aperture layer 2002. Each groove 2020 can have any suitable cross section. Although the grooves 2020 in many illustrated embodiments are shown to have a rectangular cross-section, the grooves 2020 in other embodiments may have any suitable cross-section, such as a semi-circular cross-section, oval cross-section, triangular cross-section, etc.

A groove pattern can refer to the arrangement of the grooves around a particular darkfield aperture 2010. The groove pattern can be any suitable pattern such as a circular groove pattern, a linear groove pattern, a rectangular groove pattern, an oval groove pattern, a checkerboard groove pattern, etc. Each set of adjacent grooves in a groove pattern can be separated by the same distance or can be separated by any suitable distance.

Illumination source 2040 can refer to any suitable device or other source of light such as LED, laser, white light source with a color filter, etc. The light provided by illumination source 2040 can be of any suitable wavelength and intensity. Also, the light can include polarized and/or unpolarized light. Suitable illumination sources 2040 are naturally and commercially available. In some embodiments, the illumination source 2040 can be a component of the device employing a SWEDA structure 2000. In other embodiments, the illumination source 2040 can be a separate from the device employing a SWEDA structure 2000. The illumination source 2040 can be placed in any suitable location and positioned in any suitable direction to provide appropriate light or incidence angle to the darkfield aperture 2010. In some embodiments, multiple illumination sources 2040 provide light in one or more directions. In other embodiments, a single illumination source 2040 provides light in a single direction.

Figure 20:
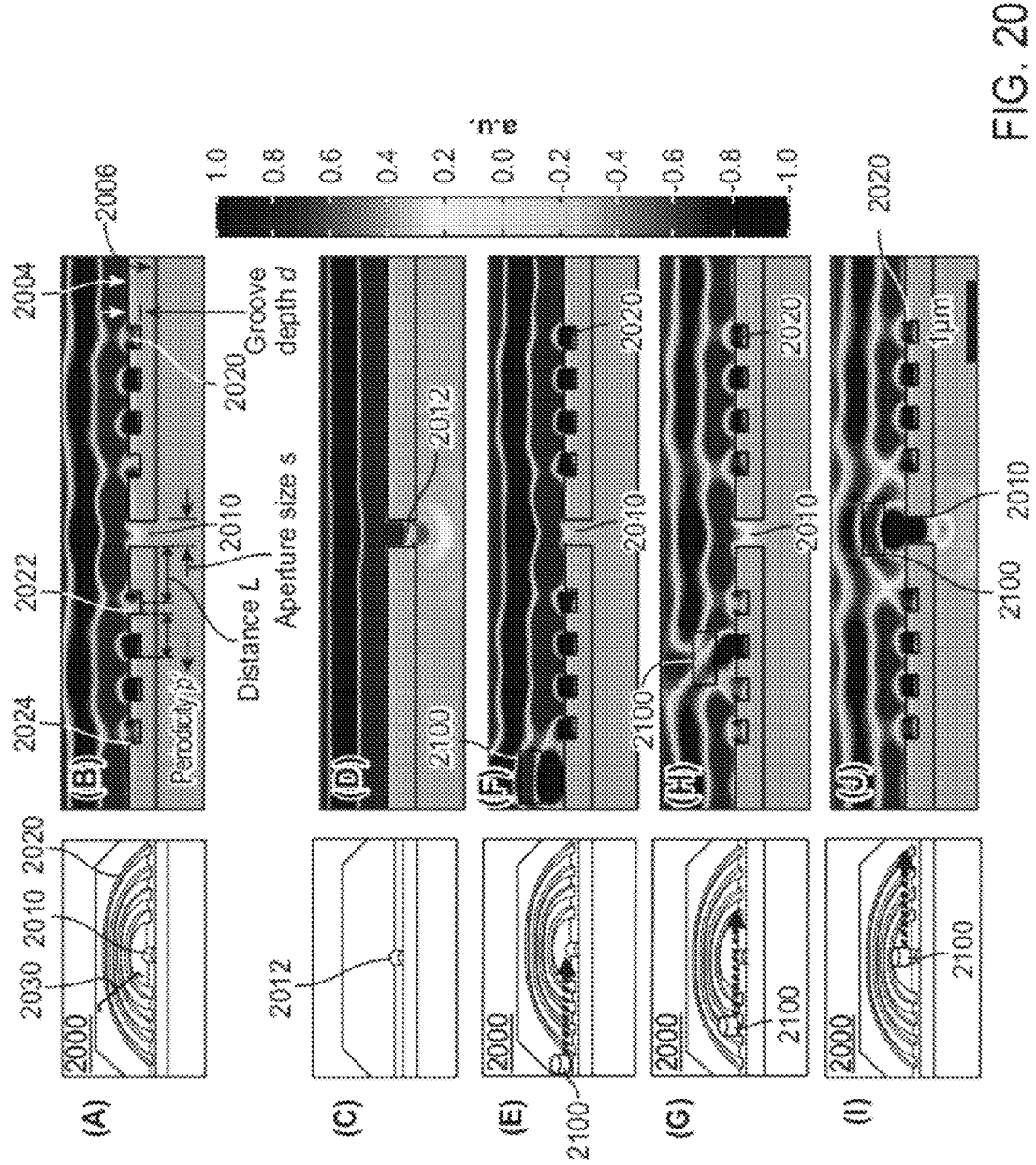
FIG. 20(A) is a schematic drawing of a portion of a SWEDA structure with a circular groove pattern, according to an embodiment of the invention.
FIG. 20(B) is a simulation of the real part of the light field around the SWEDA structure in FIG. 20(A) under uniform incident light.
FIG. 20(C) is a schematic drawing of a portion of a simple single aperture.
FIG. 20(D) is a simulation of the real part of the light field around the simple single aperture of FIG. 20(C) under uniform incident light.
FIGS. 20(E), 20(G) and 20(I) are schematic drawings showing the translation of a cylindrical dielectric object (scatterer) across a first surface of the SWEDA structure of FIG. 20(A) from the outermost groove to the darkfield aperture, according to an embodiment of the invention.
FIGS. 20(F), 20(H) and 20(J) are schematic drawings showing the translation of a cylindrical dielectric object across a first surface of the SWEDA structure of FIG. 20(A), according to an embodiment of the invention.

FIG. 20(A) is a schematic drawing of a portion of a SWEDA structure 2000 with a circular groove pattern, according to an embodiment of the invention. FIG. 20(B) is a simulation of the real part of the light field around the SWEDA structure in FIG. 20(A) under uniform incident light, according to an embodiment of the invention. FIG. 20(B) also shows some of the design features of a SWEDA structure 2000. SWEDA structure 2000 comprises a darkfield aperture 2010 having a darkfield aperture size ("s"). The SWEDA structure 2000 also includes a plurality of circular grooves 2020 that form a plurality of grooves (corrugation) 2030 around the darkfield aperture 2010. The plurality of grooves 2020 comprises a plurality of four circular grooves, including an innermost groove 2022 and an outermost groove 2024. The plurality of grooves 2020 also comprises a number of grooves ("n") equal to 4. In other cases, the SWEDA structure 2000 can have any number of grooves (e.g., 2, 5, 10, 20, etc.). Each circular groove 2020 has a groove depth ("d"). The plurality of grooves 2020 have a groove periodicity ("p") which can refer to the constant distance between adjacent grooves 2020. Although the illustrated example shows a constant distance, other embodiments may have varying distance between adjacent grooves 2020. The SWEDA structure 2000 also has a distance ("L") between the centerline of the innermost groove 2022 and the outer edge of the darkfield aperture 2010.

In many embodiments, the design features of the SWEDA structure 2000 can be optimized to maximize selected system characteristic(s) of the SWEDA structure 2000. Some examples of system characteristics can include darkfield suppression factor, enhancement factor polarization sensitivity, imaging resolution, light collection efficiency. The darkfield suppression factor refers to the ratio of the total power transmission through a simple hole (without grooves) to the total power transmission through a darkfield aperture 2010 under a uniform light field. The enhancement factor can refer to the ration of the total power transmission through the darkfield aperture 2010 to the total power transmission through a simple hole under a non-uniform light field. Another example of a system characteristic is a geometrical restriction such as overall SWEDA structure size to ensure a compact design, darkfield aperture size, groove depth, or periodicity. These geometric restrictions may be based on fabrication limitations.

The following four design parameters (features) primarily impact system characteristics (performance) of the SWEDA structure 2000: 1) groove periodicity p and groove depth d, 2) number of grooves n in the SWEDA structure 2000, 3) darkfield aperture size s and 4) distance L between the centerline of the innermost groove 2022 and the outer edge of the darkfield aperture 2010.

Groove periodicity p can refer to the distance between adjacent grooves in the SWEDA structure. Groove depth d can refer to the depth of the groove. The groove periodicity p and groove depth d can be adjusted to control the magnitude (amplitude) of the surface wave coupled in the SWEDA structure 2000. For example, the SWEDA structure 2000 can be designed so that the groove periodicity p is equal to a multiple (1, 2, etc.) of the wavelength of the surface wave to maximize the magnitude. In other examples, the groove periodicity p can be adjusted to be a distance more than or less than a multiple of the wavelength of the surface wave in order to finely tune the amplitude of the surface wave component to exactly match the amplitude of the direct transmission component. In other embodiments, other factors may be considered in selecting the groove periodicity and groove depth such as fabrication restraints.

The number of grooves, n, can refer to the number of grooves in the groove pattern around the darkfield aperture 2010 of the SWEDA structure 2000. The number of grooves n in the plurality of grooves of the SWEDA structure 2000 can also be adjusted to control the magnitude (amplitude) of the surface wave coupled into the SWEDA structure 2000. The magnitude of the coupled surface wave increases as a function of the number of grooves n. The number of grooves n also determines the size of the overall SWEDA structure 2000. In some cases, the size of the overall SWEDA structure can be limited by the density of SWEDA structures 2000 needed to provide a required image resolution. Moreover, a smaller size of the SWEDA structure 2000 may be desired for compactness considerations. These factors and other suitable factors can be considered and/or weighted in determining the number of grooves, n, in the SWEDA structure 2000.

The darkfield aperture size s can refer to dimension of the darkfield aperture. For example, the darkfield aperture size s can refer to a diameter of a circular darkfield aperture. In another example, darkfield aperture size s can refer to the length of a rectangular darkfield aperture. Although circular apertures are shown in many illustrated embodiments, other shaped apertures can be used in other embodiments. The darkfield aperture size s can be adjusted to control the magnitude (amplitude) of the direct transmission component. In addition, the darkfield aperture size s can also be restricted so that the direct light transmission is not multi-moded. Multi-mode light transmission significantly complicates the destructive interference balancing act since destructive interference between the surface wave component and the direct transmission component would have to be achieved for all modes. These factors and other suitable factors can be considered and/or weighted in determining the darkfield aperture size s.

The distance L can refer to the distance between the centerline of the innermost groove of the groove pattern and the outer edge of the darkfield aperture 2010. The distance L determines the phase of the surface wave and thus, the phase difference between the surface wave induced and the direct transmission components. To accomplish exact cancellation of the components, the distance L is selected so that the surface wave is 180 degrees out-of-phase with the direct transmission component.

In addition to these four design parameters, other design parameters can affect the system characteristics. In some cases, the type of groove pattern can affect the system characteristics. For example, the selection of a linear groove pattern can increase polarization sensitivity and/or lower darkfield suppression factor. In other cases, the type of cross-sectional profile of the grooves 2020 can also affect the system characteristics. For example, certain cross-sectional profiles do not have a sharp edge as grooves 2020, and it can be used to tune the surface wave component. However, from the fabrication point of view, the profile of the grooves 2020 is not as easy to control as other parameters. In some cases, the width and length of the grooves can also affect the system characteristics.

In some exemplary embodiments, the design features of the SWEDA structure 2000 are optimized to maximize the darkfield suppression factor to generate the most effective darkfield. In these embodiments, the features of the SWEDA structure 2000 are optimized so that the surface wave component induced by the plurality of grooves 2020 exactly balances and mutually cancels the direct transmission component of the illumination source 2040. This design maximizes the suppression factor and can result in a near-zero transmission through the darkfield aperture 2010 under uniform normal-incidence illumination from the illumination source 2040. Under non-uniform illumination, the balance between the components is disrupted and light is transmitted through the darkfield aperture 2010. In one embodiment, the features of the SWEDA structure 2000 are optimized to maximize the darkfield suppression factor and maximize the enhancement factor during non-uniform illumination conditions. In this way, the amplitude of the light transmitted through the object 2100 can be increased to provide greater contrast, which is advantageous for weak signal transmission. In another embodiment, the features of the SWEDA structure 2000 are also optimized to be sensitive to the polarization of light.

For example, the design features (parameters) of the SWEDA structure 2000 can be optimized to maximize the darkfield suppression factor by selecting design features that induce a surface wave with an amplitude equivalent (balanced) to that of the direct transmission component, and 180 degrees out of phase from the direct transmission component. In one case, the amplitude of the surface wave can be modified by changing the periodicity p and groove depth d. The aperture size s can then be selected so that the amplitude of the surface wave component is equal to the amplitude of the direct transmission component. The distance L between the innermost groove 2022 and the darkfield aperture 2010 can then be selected so that the surface wave is 180 degrees out-of-phase with the direct transmission component. In this way, the geometrical features of the SWEDA structure 2000 can be selected so that the surface wave will balance the direct transmission component under a uniform light field from an illumination source 2040. Since this condition critically depends on an exact balance of the two mentioned components, a small change in spatial distribution of the input light field intensity or phase will disrupt the destructive interference condition and permit significant light transmission through the aperture 2010. For example, an object 2100 located between the SWEDA structure 2000 and the illumination source 2040 can cause heterogeneity in the light field due to scatter which can disrupt the non-transmission condition allowing/enhancing light transmission through the darkfield aperture 2010. In this way, the design features can produce the highest suppression factor and optimal darkfield.

In the context of high sensitivity optical signal detection, the advantage of a SWEDA structure 2000 with a high suppression factor can be easily appreciated. This SWEDA structure 2000 can effectively suppress a uniform normal-incidence light from reaching the underlying sensor and instead only permit highly localized light field variations or light fields at non-zero incidence angles to pass through and be detected. As such, the underlying sensor no longer needs to contend with background light and its associated noise fluctuation terms. The bit depth can also be optimized and devoted to the detection of the weaker light field variations. Used in an appropriate manner, such devices can potentially allow for greater signal detection sensitivity in weak-signal-buried-in-high-background scenarios. This method also enables a new way to build darkfield microscopes on the sensor level that does not rely on elaborate bulky optical arrangements.

In some embodiments, a simulation program or a suitable algorithm can be used to map out the interplay of the design parameters of the SWEDA structure 2000 to one or more system characteristics. For example, the simulation program or algorithm can model the SWEDA structure 2000 and determine the behavior of the light field at the SWEDA structure 2000 due to an illumination source 2040 and/or interfering object (specimen). Exemplary simulation programs are commercially available. An example of a commercially available simulation program is CST Microwave Studio® simulation program. In one embodiment, the simulation program can be used to determine an optimal set of design parameters that will maximize/minimize one or more system characteristics (e.g., suppression factor).

In an exemplary embodiment, a simulation program was used to simulate a SWEDA structure 2000 having a set of circular grooves 2020 around a darkfield aperture 2010. The simulations were used to optimize the design parameters to maximize the suppression factor. In one case, a set of optimal design parameters was determined that maximized the suppression factor to about 6640 where the incident light field has a nominal wavelength of 738 nm. These optimal design parameters were L=774.3 nm, p=560 nm, thickness of gold=340 nm, darkfield aperture size s=300 nm, groove depth d=140 nm, and refraction index of the dielectric substrate=1.5. An example of a SWEDA structure 2000 having these optimal design parameters is shown in FIG. 20(A), 20(E), 20(G) and 20(I). The simulations of the electric field distributions around the SWEDA structure 2000 having these optimal design parameters are shown in FIGS. 20(B), 20(F), 20(H) and 20(J). FIG. 20(C) is a schematic drawing of a simple single aperture 2012. The simulation of the electric field distribution of the simple single aperture 2012 under a uniform light field is shown in FIG. 20(D).

Referring again to FIGS. 20(A) and 20(B), the illustrated SWEDA structure 2000 is under a uniform light field so that little to no light is transmitted through the darkfield aperture 2010 due to the destructive interference of the surface wave and the direct transmission components. For comparison purposes, FIG. 20(C) is a schematic drawing of a portion of a simple single aperture 2010. FIG. 20(D) is a simulation of the real part of the light field around the simple single aperture 2010 of FIG. 20(C) under uniform incident light. In comparison to the SWEDA structure 2000 in FIG. 20(D), the simulation in FIG. 20(D) shows significant transmission through the single aperture 2012. In some cases, the transmission through the simple single aperture 2012 of FIG. 20(C) can be about 1200 times larger than the transmission through the darkfield aperture 2010 in the SWEDA structure 2000 of FIG. 20(A).

FIGS. 20(E), 20(G) and 20(I) are schematic drawings showing the translation of a cylindrical dielectric object 2100 (scatterer) across a first surface 2004 of the SWEDA structure 2000 of FIG. 20(A) from the outermost groove 2024 to the darkfield aperture 2010, according to an embodiment of the invention. FIGS. 20(F), 20(H) and 20(J) are schematic drawings showing the translation of a cylindrical dielectric object 2100 across a first surface of the SWEDA structure 2000 of FIG. 20(A), according to an embodiment of the invention. In this example, the dielectric object 2100 has the following dimensions: radius 300 nm, thickness 200 nm, displacement height 300 nm, and permittivity 2.25. In other embodiments, the dielectric object 2100 can have any suitable dimensions.

Figure 21:
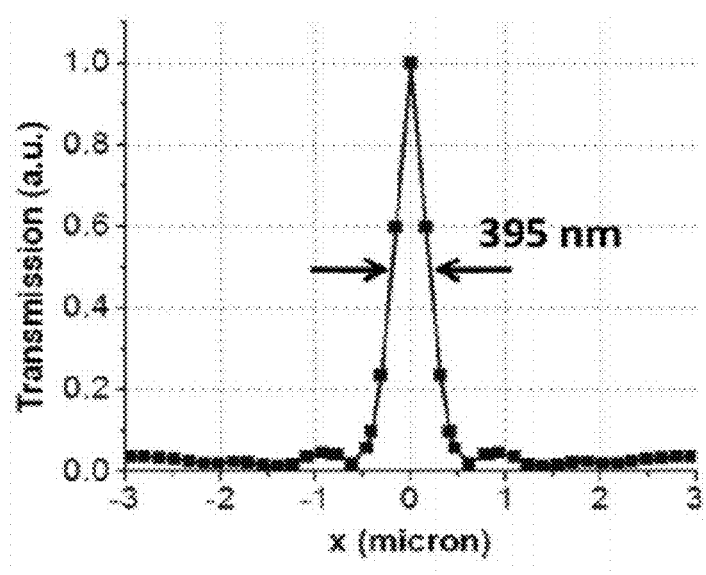
FIG. 21 is a graph of the transmission signal curve from the SWEDA structure as the scattering cylindrical dielectric object moves across a first surface of the SWEDA structure, according to an embodiment of the invention.

FIG. 21 is a graph of the transmission signal curve from the SWEDA structure as the scattering cylindrical dielectric object 2100 moves across a first surface 2004 of the SWEDA structure 2000, according to an embodiment of the invention. The graph shows the transmission through the darkfield aperture 2010 as a function of the distance of the dielectric object 2100 from the centerline of the darkfield aperture 2010. As shown in FIGS. 20(J) and 21, the SWEDA structure 2000 begins to transmit light significantly when the dielectric object 2100 is present directly above the darkfield aperture 2010. In this position, the dielectric object 2100 is significantly perturbing the direct transmission component and consequently, disrupting the delicately balanced destructive interference condition. The presence of the dielectric object 2100 adjacent to the grooves 2020 also perturbs the distribution around the center aperture 2010 to a certain extent as well, as shown in FIGS. 20(E) and 20(H). However, the impact is much less significant as shown in FIG. 20(F). This can be well appreciated by noting that the generation of a surface wave occurs over the entire area associated with the grooves 2020 and localized changes of the light field over the area have a diminished impact on the overall surface wave component. As a whole, this simulation indicates that the SWEDA structure 2000 is maximally sensitive to light field heterogeneity directly above the darkfield aperture 2010 (SWEDA).

Figure 22:
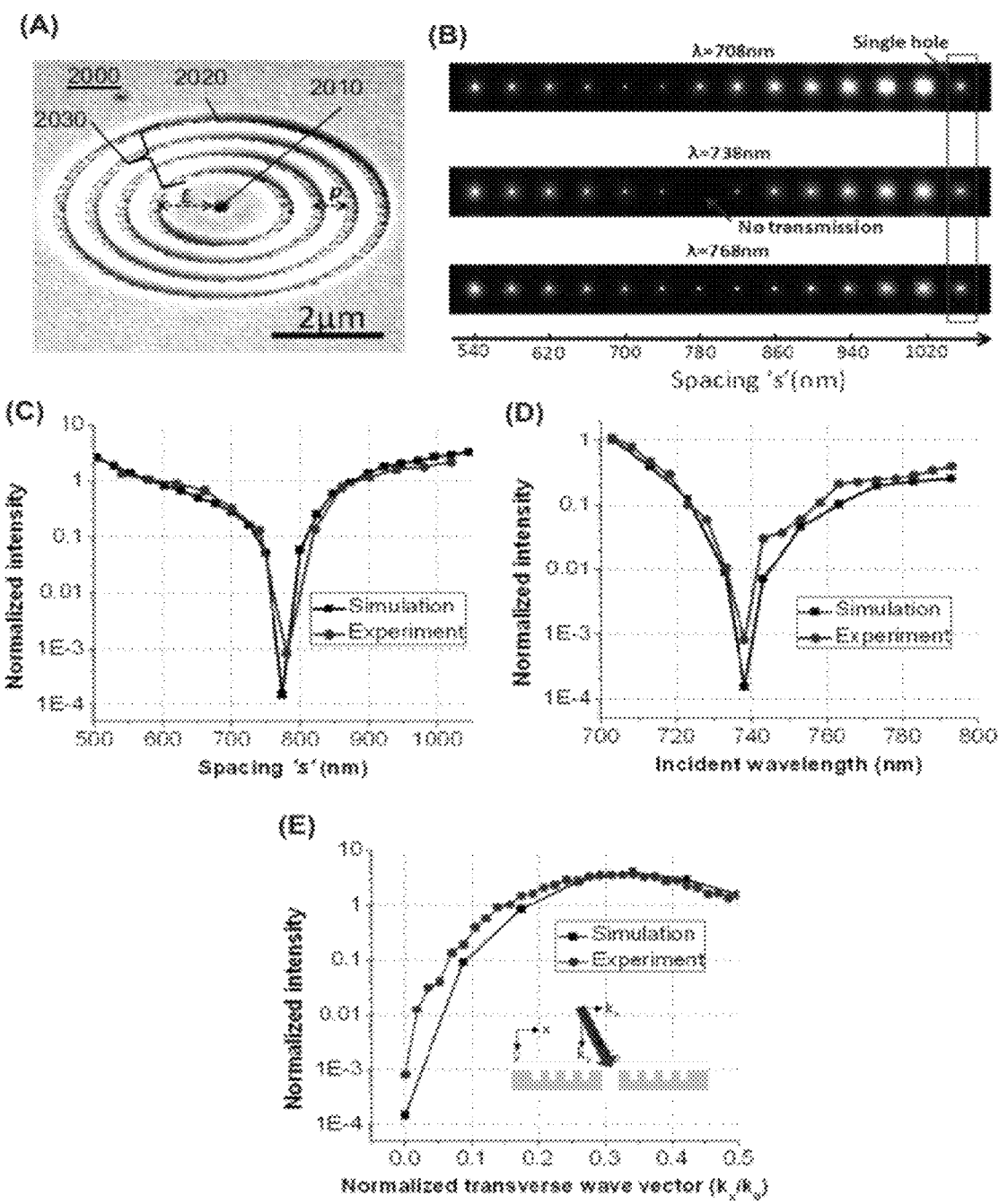
FIG. 22(A) is a scanning electron microscope image of a fabricated SWEDA structure having a circular groove pattern, according to an embodiment of the invention.
FIG. 22(B) includes the optical transmission images of thirteen (13) fabricated SWEDA structures and the reference simple single hole at normal incidence for three wavelengths: $\lambda=708$ nm, $\lambda=738$ nm and $\lambda=768$ nm, as a measure of distance L, according to an embodiment of the invention.
FIG. 22(C) is a plot of simulated and experimental normalized transmission intensity at wavelength of 738 nm for SWEDA structures having distance L ranging from 540 to 1020 nm, according to an embodiment of the invention.
FIG. 22(D) is a plot of the normalized optical transmission signals of the SWEDA structure having a distance, L=780 nm at normal incidence for three wavelengths: $\lambda=708$ nm, $\lambda=738$ nm and $\lambda=768$ nm, according to an embodiment of the invention.
FIG. 22(E) is a plot of the normalized optical transmission signals as a function of normalized traverse wave vector ($k_y/k_0$), according to an embodiment of the invention.

In one example, the affect of distance L on transmission was tested for a SWEDA structure having a circular groove pattern of an embodiment. In this example, SWEDA structures were fabricated by focus ion beam milling. The SWEDA structures 2000 in this embodiment has the optimal design parameters of periodicity p=560 nm, layer (gold) thickness=340 nm, darkfield aperture size s=300 nm, groove depth d=140 nm, and refraction index of the dielectric substrate=1.5, and a distance L ranging from 540 to 1020 nm. A simple single hole 2012 without the groove structure and having the same diameter as the darkfield aperture 2010 was also fabricated and tested as a control. A tunable wavelength laser was used as the illumination source 2040. The transmissions through the apertures were collected by an inverted microscope with a 20× objective lens. FIG. 22(A) is a scanning electron microscope image of a typical SWEDA structure 2000 fabricated in this example, according to an embodiment of the invention.

Figure 2:
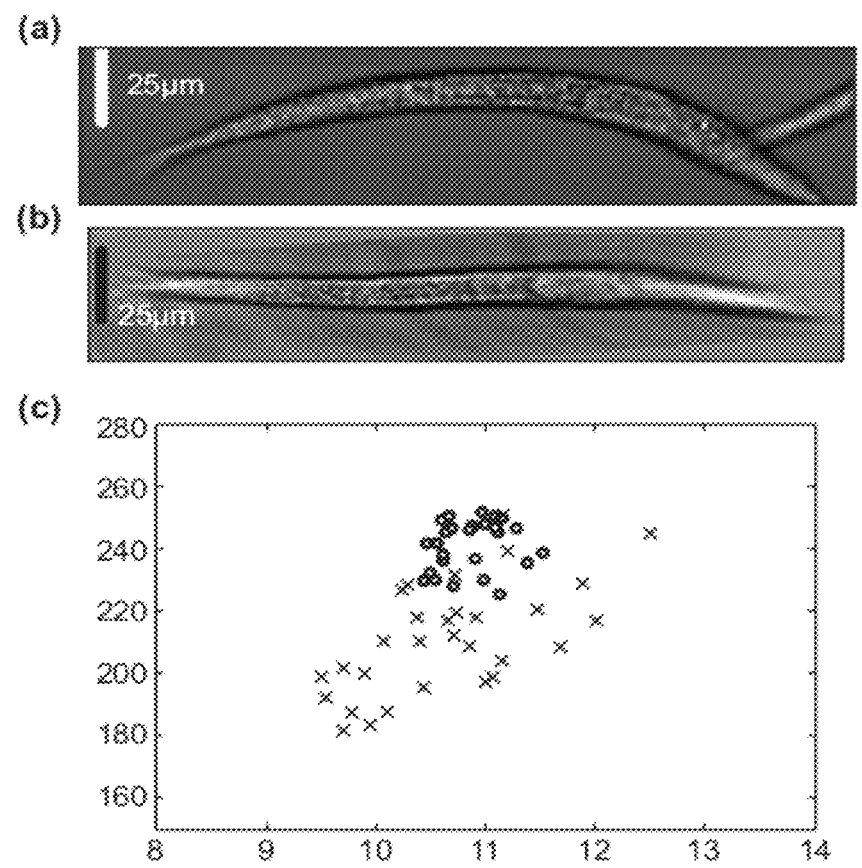
FIG. 2(a) is an illustration of an OFM image of the wild-type *C. elegans* larvae at the first larval stage.
FIG. 2(b) is an illustration of an OFM image of a dpy-24 mutant.
FIG. 2(c) is a graph illustrating the aspect ratio of wild-type larvae and dpy-24 mutants.

FIG. 22(B) shows the optical transmission images of thirteen (13) fabricated SWEDA structures 2000 and the reference simple single hole 2012 at normal incidence for three wavelengths: $\lambda=708$ nm, $\lambda=738$ nm and $\lambda=768$ nm, as a measure of distance L, according to an embodiment of the invention. As illustrated, the distance, L impacts the transmission of the SWEDA structures 2000. For each wavelength tested, a SWEDA structure 2000 with a different distance L had a minimum transmission. FIG. 2(C) is a plot of simulated and experimental transmission intensity at wavelength of 738 nm for SWEDA structures 2000 having distance L ranging from 540 to 1020 nm. From this plot, both the fabricated and simulated SWEDA structures 2000 with a distance, L=780 nm exhibited the desired near-zero transmission characteristics. The fabricated SWEDA structure 2000 had a measured suppression factor of 1230. In other words, this fabricated SWEDA 2000 structure transmitted 1230 times less light than an unadorned simple hole 2012 of size equal to that of the darkfield aperture 2020. Any discrepancy in the darkfield suppression factor between the fabricated and simulated SWEDA structures 2000 can be due to fabrication imperfections. Such imperfections could be mitigated by employing a sacrificial layer during fabrication to help preserve the sharpness of edges as described in J. Leen, et al., "Improved focused ion beam fabrication of near-field apertures using a silicon nitride membrane" Optics Letters, vol. 33, pp. 2827-2829, 2008, which is hereby incorporated by reference in its entirety for all purposes.

FIG. 22(D) is a plot of the normalized optical transmission signals of the SWEDA structure 2000 having a distance, L=780 nm at normal incidence for three wavelengths: $\lambda=708$ nm, $\lambda=738$ nm and $\lambda=768$ nm, according to an embodiment of the invention. This plot shows a single minimum transmission for each wavelength and the transmission increasing montonically away from this minimum. FIG. 22(E) is a plot of the normalized optical transmission signals as a function of normalized traverse wave vector ($k_y/k_0$), according to an embodiment of the invention. FIG. 22(E) represents the system transfer function of the SWEDA 2000 and shows that the SWEDA structure 2000 rejects the normal incident plane wave component and transmits other components with efficiency as dictated by this transfer function.

The ability to fully suppress a coherent background light as exhibited by embodiments of circular-groove based SWEDA structures 2000 can be useful for small signal detections in metrology applications. It is especially applicable in detection scenarios where the overall background intensities fluctuate with time. As our background subtraction occurs at the individual pixel level, SWEDA technology removes the need for balanced detection schemes. The pre-detection background subtraction, which is a light cancellation process, is also intrinsically more sensitive than post-detection cancellation schemes that are susceptible to intrinsic detection statistical variations. The inclusion of chemical reagents in the darkfield aperture 2010 can also turn such a SWEDA structure 2000 into a high-sensitivity sensor that can react to small refractive index changes of the reagents.

D. SWEDA Structure with a Linear Groove Pattern

Embodiments of SWEDA structures 2000 with grooves in a linear groove pattern can be highly sensitive to the polarization state of the incident light. In some cases, SWEDA structures 2000 having linear groove patterns can be designed to serve as a highly compact and highly efficient polarization sensor.

Figure 23:
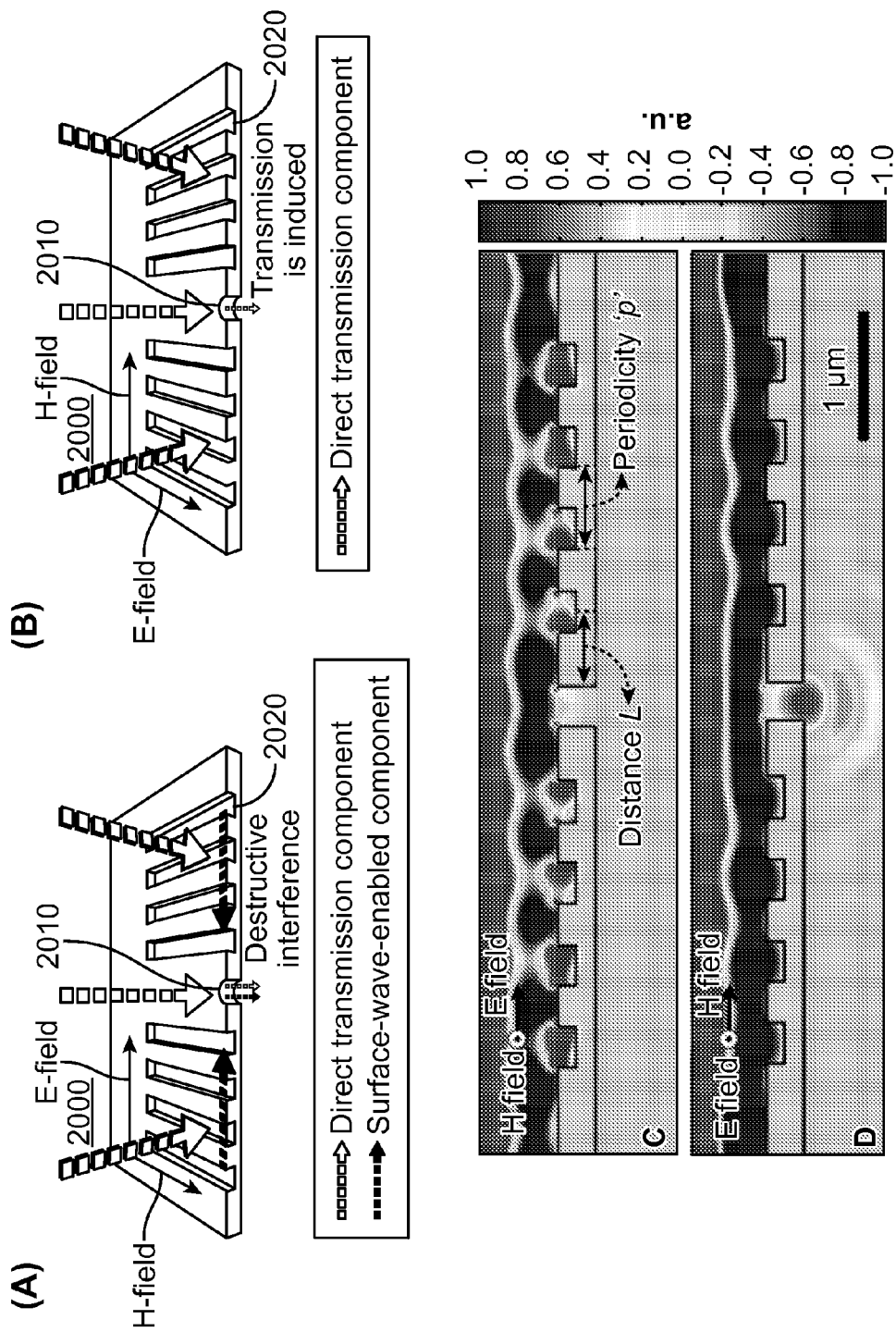
FIGS. 23(A) and 23(B) are schematic drawings of a portion of a SWEDA structure with grooves in a linear pattern, according to an embodiment of the invention.
FIG. 23(C) is a simulation of the TM case of a SWEDA structure having a linear groove pattern, according to an embodiment of the invention.
FIG. 23(D) also shows the show the electric-field distributions for the TE wave, from which we can see that the structure does transmit TE wave significantly, according to an embodiment of the invention.

FIG. 23(A) is a schematic drawing of a portion of a SWEDA structure 2000 with grooves in a linear pattern, according to an embodiment of the invention. The SWEDA structure 2000 includes a layer having a plurality of eight linear grooves 2020, four on each side of a central darkfield aperture 2010. Other embodiments can have more or fewer linear grooves 2020. FIG. 23(A) illustrates that incoming TM polarized light can be collected and converted into a surface wave by the periodic grooves 2020 and then be recoupled into propagating light through the central aperture 2010. TM polarized light refers to light where the electric field is perpendicular to the groove structure. TE polarized light refers to light where the electric field is along the groove structure. FIG. 23(B) illustrates that that the incoming TE polarized light cannot be as effectively coupled into surface waves and transmission is induced in the absence of destructive interference.

FIG. 23(C) is a simulation of the TM case of a SWEDA structure 2000 having a linear groove pattern, according to an embodiment of the invention. The simulation shows the real part of the electric-field at $\lambda=750$ nm. In this embodiment, the SWEDA structure 2000 has optimal design parameters of distance L=658 nm, periodicity p=658 nm, layer (gold) thickness=340 nm, darkfield aperture size s=300 nm, groove depth d=140 nm, and refraction index of the dielectric substrate=1.5. In this embodiment, the TM darkfield suppression factor of the simulated SWEDA structure 2000 of this embodiment was 35,400. The TM case is described in Maier, S., "Plasmonics: fundamentals and applications," Springer Verlag, 2007, which is hereby incorporated by reference in its entirety for all purposes. FIG. 23(D) is a simulation of the TE case of the SWEDA structure 2000 of FIG. 23(C). The simulation shows the real part of the magnetic field at $\lambda=750$ nm. The simulation predicts the polarization extinction ratio of the two orthogonal polarization states is 42500. FIG. 23(D) also shows the show the electric-field distributions for the TE wave, from which we can see that the structure does transmit TE wave significantly, according to an embodiment of the invention. The difference between the TM and TE cases also verifies the surface-wave-enabled mechanism of the linear-groove based SWEDA, since the SP wave can only be induced efficiently for TM polarization. From the simulations shown in FIGS. 23(C) and 23(D), the linear-groove based SWEDA structure 2000 provides a polarization extinction ratio of 42500 for the two orthogonal polarization states.

Figure 24:
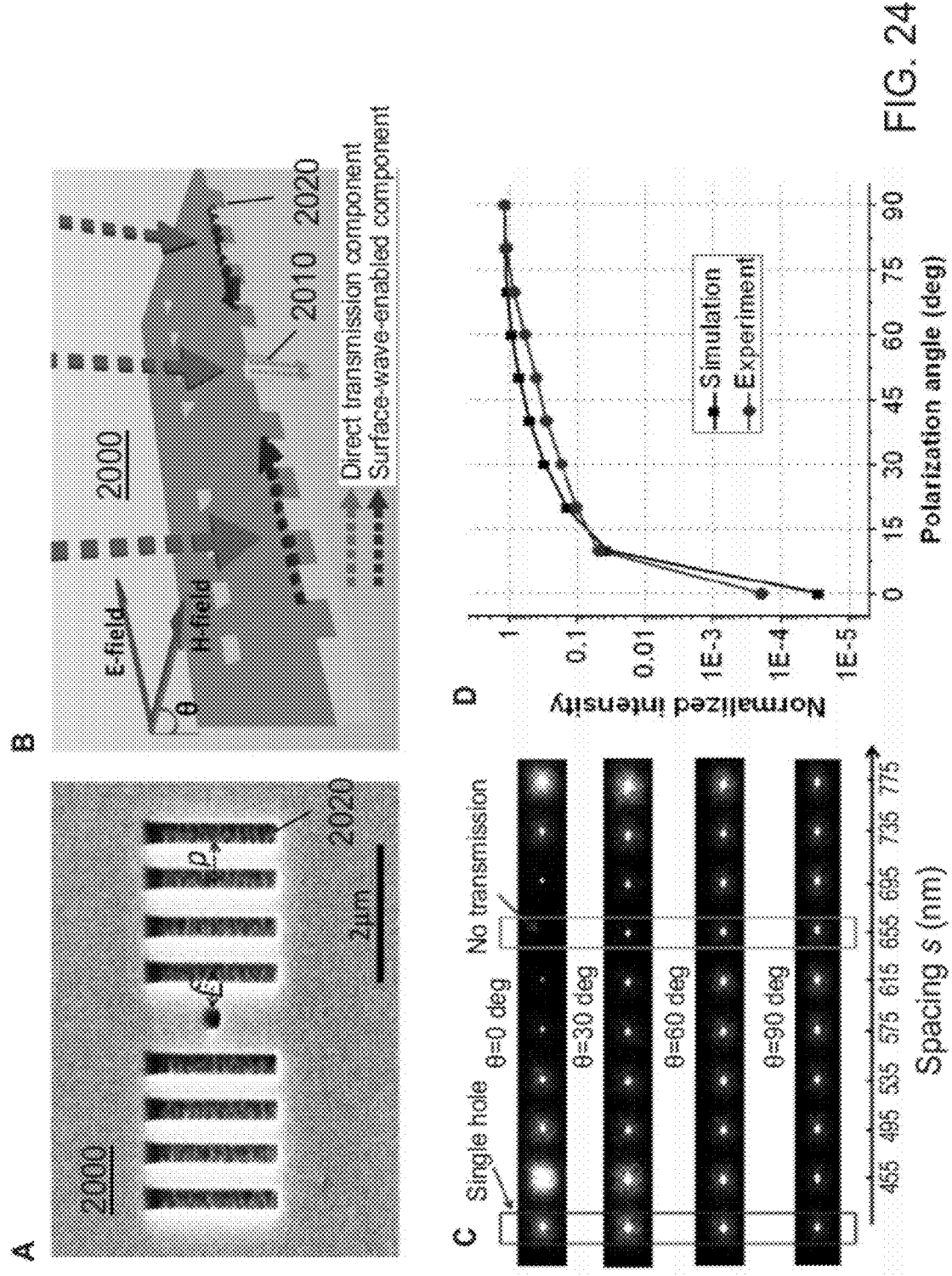
FIG. 24(A) is a scanning electron microscope image of a typical fabricated SWEDA structure with a linear groove pattern, according to an embodiment of the invention.
FIG. 24(B) is a schematic drawing of light incident with a polarization angle ("θ") on a SWEDA structure having a linear groove pattern.
FIG. 24(C) shows the optical transmission images the nine (9) SWEDA structures having a linear groove pattern for different polarization angles at wavelength of 750 nm and the reference simple single hole at normal incidence for four different polarization angles: θ=0 degrees; θ=30 degrees; θ=60 degrees; and θ=90 degrees, according to an embodiment of the invention.
FIG. 24(D) is a graph of the normalized optical transmission signals of the SWEDA structures with a linear groove pattern plotted as a function of polarization angle, in accordance with an embodiment of the invention.

In one example, the affect of distance L on transmission was tested for a SWEDA structure 2000 having a linear groove pattern of an embodiment of the invention. In this example, nine (9) SWEDA structures having a linear groove pattern of this embodiment were fabricated by FIB milling. FIG. 24(A) is a scanning electron microscope image of a typical fabricated SWEDA structure with a linear groove pattern, according to an embodiment of the invention. The SWEDA structures 2000 in this embodiment had distances, L ranging from 455 nm to 775 nm. FIG. 24(B) is a schematic drawing of light incident with a polarization angle ("θ") on a SWEDA structure 2000 having a linear groove pattern, according to an embodiment of the invention.

FIG. 24(C) shows the optical transmission images the nine (9) SWEDA structures 2000 having a linear groove pattern for different polarization angles at wavelength of 750 nm and the reference simple single hole 2012 at normal incidence for four different polarization angles: θ=0 degrees; θ=30 degrees; θ=60 degrees; and θ=90 degrees, according to an embodiment of the invention. FIG. 24(D) is a graph of the normalized optical transmission signals of the SWEDA structures 2000 with a linear groove pattern plotted as a function of polarization angle, in accordance with an embodiment of the invention. In one case, the measured polarization extinction ration for TE and TM incidence was 6100 so that that the amount of TE light transmission through the linear-groove based SWEDA structure 2000 is 6100 times higher than the TM case. Such a high extinction ratio positively indicates that the linear-groove based SWEDA structure 2000 can serve as a highly compact and highly efficient polarization sensor.

In some exemplary embodiments, a SWEDA structure 2000 with grooves in a linear groove pattern is used as a polarization sensor. Since the polarization state of light will change during the interaction with chiral materials, this SWEDA structure 2000 can find some applications in on-chip detection of some chiral materials such as sugar, proteins and DNA as can be found in G. Fasman, Circular dichroism and the conformational analysis of biomolecules: Plenum Pub Corp, 1996, and in K. Minakawa, et al., "Microchamber Device Equipped with Complementary Metal Oxide Semiconductor Optical Polarization Analyzer Chip for Micro Total Analysis System," Jpn. J. Appl. Phys., vol. 48, p. 04 C192, 2009, which are hereby incorporated by reference in their entirety for all purposes.

D. SWEDA Structure for Boosting Detection Sensitivity

Some embodiments of SWEDA structures 2000 can be designed with optimal design features to improve detection of signals, especially weak signals. In these embodiments, the design features are optimized to increase the amplitude of the direct transmission component. For example, the size of the darkfield aperture 2010 may be increased. In one exemplary embodiment, a SWEDA structure 2000 can be designed with optimal design features to both generate a darkfield under a uniform light field and boost the direct transmission signal under a non-uniform light field.

In one embodiment, a SWEDA structure 2000 having an optimized circular groove pattern was used to perform raster-scanning in a relay microscope. A uniform light field of intensity of about 0.2 W/cm$^2$ from a 738 nm laser was transmitted through each specimen. A 1:1 relay microscope was used to project a virtual image of the specimen onto the optimized circular-groove based SWEDA structure 2000. An example of a 1:1 relay microscope can be found in X. Cui, et al., "Quantitative differential interference contrast microscopy based on structured-aperture interference," Applied Physics Letters, vol. 93, p. 091113, 2008, which is hereby incorporated by reference in its entirety for all purposes. The specimen was raster scanned. The light transmission through the darkfield aperture 2010 was measured at each point of the scan. A darkfield image was generated by compiling the collected data. A similar image was taken with a standard microscope for comparison.

Figure 25:
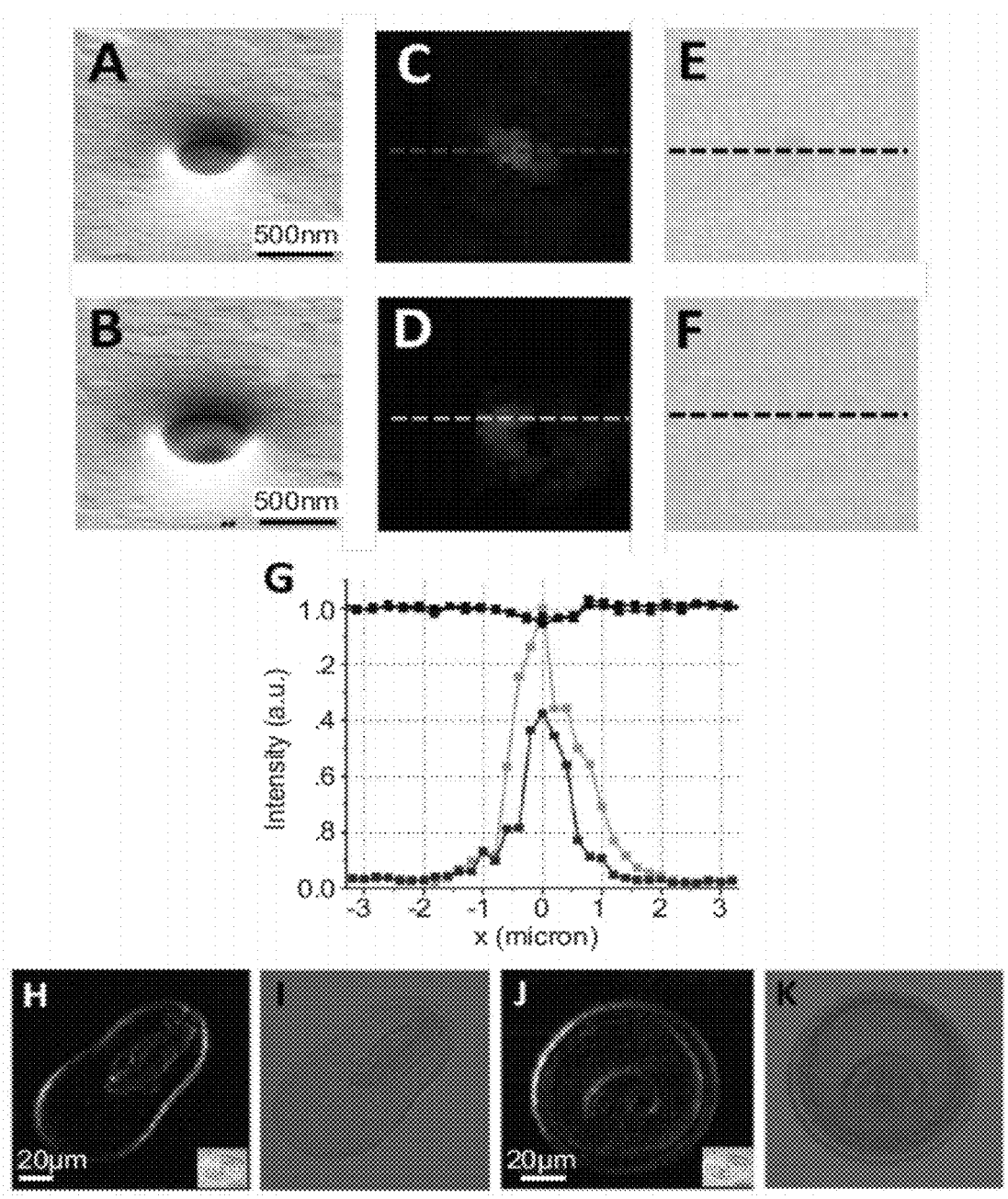
FIGS. 25(A) and 25(B) are scanning electron microscope images of the 175 and 250 nm pits respectively, in accordance with an embodiment of the invention.
FIGS. 25(C) and 25(D) are images taken of the 175 and 250 nm pits using a SWEDA-based raster-scanning device, in accordance with an embodiment of the invention.
FIGS. 25(E) and 25(F) are images of the 175 and 250 nm pit samples taken using a conventional camera with the same CMOS chip under the same illumination condition as the SWEDA collected images in FIGS. 25(C) and 25(D).
FIG. 25(G) is a graph of the signal traces of the intensity readings across a centerline of the two pits for the SWEDA based device, according to an embodiment of the invention and the conventional camera.
FIGS. 25(H) and 25(J) are SWEDA-based raster-scanned images of starfish embryos, according to an embodiment of the invention.
FIGS. 25(I) and 25(K) are images of the starfish embryos taken by a conventional bright field microscope.

In one case, a specimen was prepared of ITO-coated glass slide that was marked with shallow pits of radius of 175 nm and 250 nm via the FIB. FIGS. 25(A) and 25(B) are scanning electron microscope images of the 175 and 250 nm pits respectively, in accordance with an embodiment of the invention. FIGS. 25(C) and 25(D) are images taken of the 175 and 250 nm pits using a SWEDA-based raster-scanning device, in accordance with an embodiment of the invention. FIGS.

25(E) and 25(F) are images of the 175 and 250 nm pit samples taken using a conventional camera with the same CMOS chip under the same illumination condition as the SWEDA collected images in FIGS. 25(C) and 25(D).

FIG. 25(G) is a graph of the signal traces of the intensity readings across a centerline of the two pits for the SWEDA based device of an embodiment of the invention and the conventional camera. The measured image contrast (signal/background) enhancement is approximately 25 dB for the 175 nm pit and approximately 27 db for the 250 nm pit. The data acquired for the SWEDA-based device was normalized on the same scale. The conventional camera data was normalized versus the average background signal. The background intensity associated with the SWEDA-based device data was low and the contributive signals from the pits were well discernible. In fact, the contributive signals were sufficiently well-resolved that we can use them to quantify their relative strengths for the two pits. In comparison, the high background intensity of the conventional camera images combined with the associated noise masked the scattering contributions from the pits.

FIGS. 25(H) and 25(J) are SWEDA-based raster-scanned images of starfish embryos, according to an embodiment of the invention. FIGS. 25(I) and 25(K) are images of the starfish embryos taken by a conventional bright field microscope. The SWEDA based device images shown in FIGS. 25(H) and 25(J) have a dark background. In addition, the edge and interior of the starfish embryos appeared brighter in the SWEDA images shown in FIGS. 25(H) and 25(J) and darker in the control image shown in FIGS. 25(I) and 25(K). That is, the device employing the SWEDA structure 2000 generated an image with a dark background while producing an image where the edge and interior of the starfish embryo appears brighter, with higher contrast as opposed to the control image which is darker with less contrast. This is again consistent with a darkfield image as sample locations with substantial scattering will appear brighter in a darkfield image than a simple transmission microscope.

In some embodiments a circular-groove based SWEDA structure 2000 can be employed to perform darkfield microscopy imaging at the sensor level. As explained in sections above, the underlying principle of a microscope employing a SWEDA structure 2000 is different from that of a conventional darkfield microscope. Conventional darkfield microscopy depends on oblique illumination and a relatively small objective angle of collection to screen out the uniform background via a fairly sophisticated bulk optical arrangement. The ability of a circular-groove based SWEDA structure 2000 to screen out uniform background presents a more direct approach.

In many embodiments, SWEDA structures 2000 have features that are optimized for single wavelength operations. In other embodiments, a SWEDA structure 2000 can include a multibeam interference that can operate over a broad range of wavelengths. In these embodiments, the features of the SWEDA structure 2000 with the multibeam interference can be optimized to operate for a broad range of wavelengths.

In many embodiments, the SWEDA structures 2000 are designed with symmetric features to block out only uniform light at normal incidence. In other embodiments, the SWEDA structure may have assymetric features such as a darkfield aperture and/or grooves with asymmetric structure that can screen out light at other incidence angles.

In some embodiments, SWEDA structures 2000 can be fabricated on top of a CCM or CMOS sensor pixels. The small size and substantially planar design of SWEDA structures 2000 of certain embodiments can make such implementation particularly suited for foundry fabrication.

In one embodiment, an array of SWEDA structures 2000 can replace an array of simple light transmissive regions in an optofluidic microscope (OFM) device-a low-cost, lensless and high resolution microscopy approach, to accomplish darkfield microscopy imaging on a chip. Examples of OFM devices can be found in X. Cui, et al., "Lensless high-resolution on-chip optofluidic microscopes for *Caenorhabditis elegans* and cell imaging," Proceedings of the National Academy of Sciences, vol. 105, p. 10670, 2008 and X. Heng, et al., "Optofluidic microscopy—method for implementing a high resolution optical microscope on a chip," Lab on a Chip, vol. 6, pp. 1274-1276, 2006, which are hereby incorporated by reference in their entirety for all purposes. The use of SWEDA structures 2000 in this embodiment is especially appropriate as both the OFM device and SWEDA structure implementation are well suited for semiconductor mass-fabrication. In fact, it is difficult to envision a more compact and cost-effective approach for incorporating darkfield ability than in an OFM system.

In some exemplary embodiments, a SWEDA structure 2000 exactly balances the surface-wave-induced component and direct light transmission component in a destructive interference manner. In one embodiment, the SWEDA structure 2000 acts effectively as a tiny interferometer (~6 microns or less) that can be fabricated on a single metal substrate and which has excellent stability. In many cases, SWEDA structures 2000 exhibit little to no significant performance drift over an entire operation. Further, since SWEDA structures are planar or substantially planar in many cases, they can be mass produced in a semiconductor foundry.

D. SWEDA Based Implementations and Applications

In some embodiments, SWEDA based systems can effectively suppress the background prior to sensor detection and allow detection of weak signals in extremely compact architectures. These SWEDA based system can be advantageous for a broad range of applications from on-chip bio-sensing to metrology and microscopy.

For example, a SWEDA structure 2000 can be fabricated onto a sensor chip (e.g., CMOS sensor chip) which can be easily implemented by plugging it into an imaging device (e.g., standard microscope) to generate a darkfield microscope. In one case, the sensor chip can be patterned with a grid of tightly spaced circular groove based SWEDA structures 2000 that can be used as the microscope camera. The darkfield microscope can employ a laser as an illumination source 2040.

Figure 26:
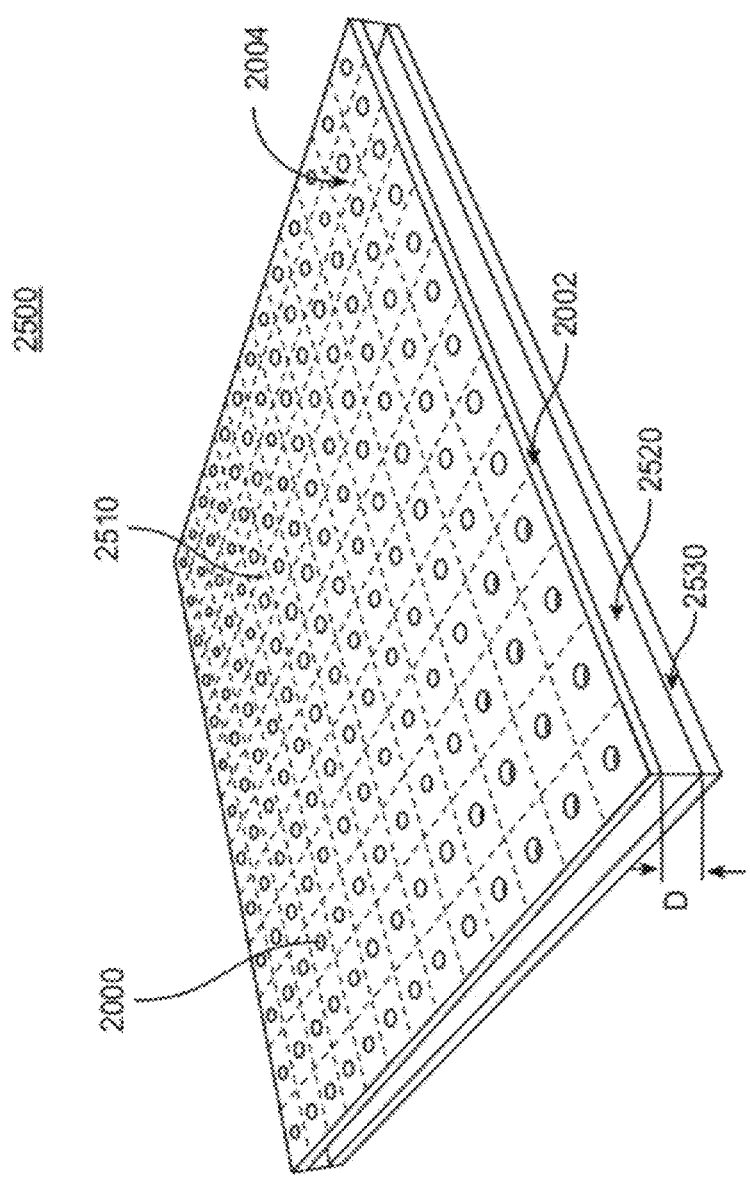
FIG. 26 is a schematic drawing of a SWEDA based system having a SWEDA-based sensor, according to an embodiment of the invention.

FIG. 26 is a schematic drawing of a SWEDA based system 2500 having a SWEDA-based sensor 2510, according to an embodiment of the invention. The SWEDA based sensor comprises an aperture layer 2002, a light detector 2530, and a transparent layer 2520 between the aperture layer 2002 and the light detector 2530. In other embodiments, the SWEDA based sensor 2510 does not have a transparent layer 2520.

The aperture layer 2002 is located at a distance D away from the light detector 2530. The transparent layer 2520 between the light detector 2530 and the aperture layer 2002 can include one or more layers of transparent material such as water or a viscous polymer (e.g., SU-8 resin), or can be a vacuum or gas-filled space.

The aperture layer 2002 has a first surface 2004 and a second surface 2006 (not shown). The aperture layer 2002 also includes a plurality of SWEDA structures 2000 arranged in a two dimensional array of SWEDA structures 2000 in the first surface 2004. In this case, the aperture layer 2002 can be made of silver and has a thickness of 350 nm. In other cases, the aperture layer 2002 can be made of gold plated glass plate. Although a two-dimensional array is shown in this embodiment, any suitable arrangement of SWEDA structures 2000 can be used in other embodiments of a SWEDA system 2500. Some examples of suitable arrangements include a one-dimensional array, multiple one-dimensional arrays, a set of circular rings of SWEDA structures 2000, etc. In addition, any suitable number of SWEDA structures 2000 can be used in the SWEDA system 2050. Further, any suitable spacing between the SWEDA structures 2000 can be used.

The light detector 2530 (e.g., photosensor) can refer to any suitable device capable of measuring the distribution of light received through the darkfield apertures 2010 in the SWEDA structures 2000 and capable of generating signals with wavefront data about the intensity, wavelength, wavefront slope, phase gradient in one or more orthogonal directions, and/or other information about the light being detected. The signals may be in the form of electrical current that results from the photoelectric effect. Some examples of suitable light detectors 2530 include a charge coupled device (CCD) or a linear or two-dimensional array of photodiodes (e.g., avalanche photodiodes (APDs)). A light detector 2530 could also be a complementary metal-oxide-semiconductor (CMOS) or photomultiplier tubes (PMTs). Other suitable light detectors 2530 are commercially available.

The light detector 2530 comprises one or more light detecting elements 2532. The light detecting elements 2530 can be of any suitable size (e.g., 1-4 microns) and any suitable shape (e.g., circular or square). The light detecting elements 2530 can be arranged in any suitable form such as a one-dimensional array, a two-dimensional array, and a multiplicity of one-dimensional and/or two-dimensional arrays. The arrays can have any suitable orientation or combination of orientations. In some cases, the light detecting elements 2530 can be arranged in the same form as the darkfield apertures 2010 and correspond to the darkfield apertures 2010.

In one embodiment, sensor chips with SWEDA-based sensors 2510 having broad-bandwidth SWEDA structures 2000 can be used in place of the standard camera sensor to accomplish sensor level darkfield imaging. Such sensor chips, in combination with a coherent light source, can transform a standard microscope into a darkfield microscope that is simpler and less expensive than current darkfield microscopes. Such sensor chips can also be used to enable edge-detection imaging in machine vision applications if the illumination source employed is coherent.

In some embodiments, the illumination source of a SWEDA based device 2500 can be altered to modify the direct transmission component so that it has the same amplitude and phase of a surface wave induced by an existing SWEDA structure 2000. In these embodiments, the phase and amplitude of the direct transmission component is modified to match the phase and amplitude of the surface wave component. In one embodiment, the incident angle of the incident angle of the illumination source 2040 is modified so that the amplitude and phase of the direct transmission component is similar to the surface wave induced by an already existing SWEDA structure 2000. For example, the incident angle can be modified by degrees until a predetermined or measurable improvement is made in the darkfield. In some cases, this technique can be used to fine tune a SWEDA based device 2500 with already fabricated SWEDA structures 2000. In one exemplary embodiment, this technique can be used to calibrate a SWEDA based device 2500. This technique can be used alone or in combination with the method of modifying the design features of the SWEDA structure 2000 to induce a surface wave which is equal to the direct transmission of an illumination source.

SWEDA structures 2000 according to embodiments and SWEDA based sensors 2510 having SWEDA structures 2000 according to some embodiments, can be fabricated in any suitable manner. An exemplary method for fabricating a SWEDA based sensor 2510 having a single SWEDA structure 2000 according to an embodiment can be described with reference to FIGS. 27(a)-27(d). In these figures, the darkfield aperture 2010 is a hole. Any suitable combination of well know processes including etching, lamination, and photo lithography can be used to fabricate the SWEDA structures 2000 and SWEDA based sensors 2510 according to some embodiments.

In some cases, the aperture layer 2002 may consist of a metal layer and a transparent plate (e.g., a glass plate). In these cases, the metal layer can be evaporated onto the transparent surface of the transparent plate in some embodiments. Alternatively, the aperture layer 2002 can be of any other suitable opaque or semi-opaque layer.

Figure 27:
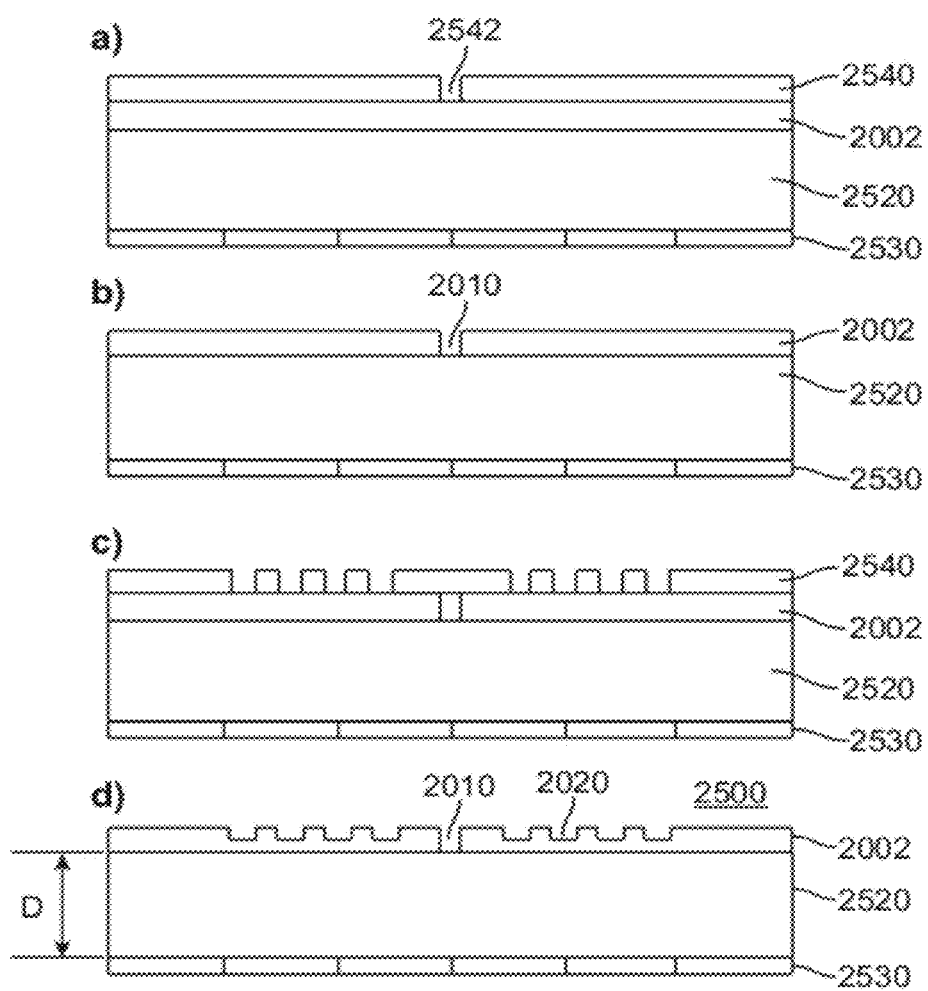
FIGS. 27(a)-27(d) illustrate a process of fabricating a SWEDA based sensor, according to an embodiment of the invention.

As shown in FIG. 27(a), a first photo resist layer 2540 having a hole 2542 is placed on the aperture layer 2002 (e.g. a gold layer), according to an embodiment of the invention. A transparent layer 2520 is attached to the aperture layer 2000. Also, a light detector 2530 including discrete light detecting elements is attached to the transparent layer 2530.

An etching process or other suitable process is used to form a darkfield aperture 2010 in the aperture layer 2002. Any suitable process such as standard electron beam lithography can be used to generate the hole in the first photo resist layer 2540. In other embodiments, etching need not be used. For example, laser ablation can be used to form darkfield aperture 2010 in the aperture layer 2002.

In FIG. 27(b), the photo resist layer 2540 is removed. In FIG. 27(c), a new second photo resist layer 2550 is deposited on the aperture layer 2002. Any suitable type of transparent or semi-transparent material can be used in the first and second photo resist layers 2540 and 2550. The second photo resist layer 2550 includes channels through the layer that are in the shape of the desired grooves 2020 of the SWEDA structure 2000.

An etching process can be used to form the grooves 2020 in the aperture layer 2002. In FIG. 27(d), the second photo resist layer 2550 is removed, forming the SWEDA based sensor 2500, according to an embodiment of the invention. The SWEDA based sensor 2500 comprises the SWEDA structure 2000, the light detector 2530 and the transparent layer 2520 between the light detector 2530 and the aperture layer 2002.

In one embodiment, a sacrificial layer (e.g., a 1000 nm thick silicon nitride layer) can coat the aperture layer 2002. The first and second photo resist layers 2540 and 2550 can be deposited onto of this sacrificial layer. After the darkfield aperture 2010 and the grooves 2020 are created, the sacrificial layer can be removed. By employing the sacrificial layer, the SWEDA structure 2000 may have sharper features. In some cases, the SWEDA structure 2000 of this embodiment can provide better system characteristics such as a higher darkfield suppression factor.

As an example of other potential applications, the concept of the SWEDA structure 2000 can be applied to optical isolation in a ultra-compact format, polarization control in semiconductor lasers, wavefront detection, extending depth of field of the type II aperture based imaging device, and perspective imaging by customizing the optical transfer function on the pixel level. An example of a semiconductor laser can be found in N. Yu, et al., "Semiconductor lasers with integrated plasmonic polarizers," Applied Physics Letters, vol. 94, p. 151101, 2009, which is hereby incorporated by reference in its entirety for all purposes. An example of a type II aperture based imaging device can be found in X. Heng, et al., "Characterization of light collection through a subwavelength aperture from a point source," Optics express, vol. 14, pp. 10410-10425, 2006, which is hereby incorporated by reference in its entirety for all purposes. An example of perspective imaging can be found in R. Ng, et al., "Light field photography with a hand-held plenoptic camera," Computer Science Technical Report CSTR, vol. 2, 2005, which is hereby incorporated by reference in its entirety for all purposes.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

A recitation of "a", "an" or "the" is intended to mean "one or more" unless specifically indicated to the contrary.

The above description is illustrative and is not restrictive. Many variations of the disclosure will become apparent to those skilled in the art upon review of the disclosure. The scope of the disclosure should, therefore, be determined not with reference to the above description, but instead should be determined with reference to the pending claims along with their full scope or equivalents.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

All patents, patent applications, publications, and descriptions mentioned above are hereby incorporated by reference in their entirety for all purposes. None is admitted to be prior art.

What is claimed is:

1. A surface wave enabled darkfield aperture structure comprising:
    an aperture layer having a first surface and a second surface, wherein a surface wave propagates along the first surface;
    an aperture in the aperture layer;
    a plurality of grooves in the first surface around the aperture, the plurality of grooves configured to generate a darkfield at the aperture by modifying the surface wave to cancel out direct transmission of a uniform incident light field received by the aperture.

2. The surface wave enabled darkfield aperture structure of claim 1, wherein the plurality of grooves is further configured to pass light of a non-uniform light field through the aperture.

3. The surface wave enabled darkfield aperture structure of claim 1, wherein the surface wave is modified to be about 180 degrees out of phase from the direct transmission.

4. The surface wave enabled darkfield aperture structure of claim 1, wherein the surface wave is modified to be similar in amplitude to the direct transmission.

5. The surface wave enabled darkfield aperture structure of claim 1, wherein the aperture and the plurality of grooves are configured to enhance light passed through the aperture under a non-uniform light field.

6. The surface wave enabled darkfield aperture structure of claim 1, wherein the aperture and the plurality of grooves are configured to enhance light passed through the aperture when a non-homogenous object disrupts the uniform light field.

7. The surface wave enabled darkfield aperture structure of claim 1, wherein the aperture and the plurality of grooves are configured to modify the direct transmission based on a degree if polarity of the uniform light field.

8. The surface wave enabled darkfield aperture structure of claim 1, wherein the aperture has a darkfield suppression factor of at least 1000.

9. The surface wave enabled darkfield aperture structure of claim 1, wherein each of the plurality of grooves is circular.

10. The surface wave enabled darkfield aperture structure of claim 1, wherein at least one of the plurality of grooves is linear.

11. The surface wave enabled darkfield aperture structure of claim 1, further comprising a second plurality of grooves in the second surface of the aperture layer, wherein the second plurality of grooves modifies a second surface wave propagated along the second surface.

12. A surface wave enabled darkfield aperture sensor comprising:
    an aperture layer having a first surface and a second surface, wherein a surface wave propagates along the first surface;
    a plurality of apertures in the aperture layer;
    a plurality of grooves in the first surface around each corresponding aperture, the plurality of grooves configured to generate a darkfield at the aperture by modifying the surface wave to cancel out direct transmission of a uniform incident light field received by the aperture; and
    a light detector adapted to detect light passing through the apertures.

13. The surface wave enabled darkfield aperture sensor of claim 12, wherein the plurality of grooves is further configured to pass light of a non-uniform light field through the corresponding aperture.

14. The surface wave enabled darkfield aperture sensor of claim 12, further comprising a transparent layer between the aperture layer and the light detector.

15. The surface wave enabled darkfield aperture sensor of claim 12, wherein the plurality of apertures is arranged in a two-dimensional array.

* * * * *

UNITED STATES PATENT AND TRADEMARK OFFICE
CERTIFICATE OF CORRECTION

PATENT NO.       : 8,189,204 B2  
APPLICATION NO.  : 12/792059  
DATED            : May 29, 2012  
INVENTOR(S)      : Cui et al.

Page 1 of 1

It is certified that error appears in the above-identified patent and that said Letters Patent is hereby corrected as shown below:

Col. 1, lines 46-49;

Delete under Government Interests:

"The U.S. Government has certain rights in this invention pursuant to Grant No. HR0011-04-1-0032 awarded by DARPA and pursuant to Grant No. EB008867 awarded by NIH."

Add under Government Interests:

"This invention was made with government support under Grant No. EB008867 awarded by the National Institutes of Health and under Grant No. HR0011-04-1-0032 awarded by DARPA. The government has certain rights in the invention."

Signed and Sealed this  
Thirteenth Day of November, 2012

David J. Kappos  
*Director of the United States Patent and Trademark Office*

UNITED STATES PATENT AND TRADEMARK OFFICE
Certificate

Patent No. 8,189,204 B2                                                                  Patented: May 29, 2012

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Xiquan Cui, Pasadena, CA (US); Xin Heng, Somerville, MA (US); Changhuei Yang, Pasadena, CA (US); Axel Scherer, Laguna Beach, CA (US); and Guoan Zheng, Pasadena, CA (US).

Signed and Sealed this Twenty-sixth Day of March 2013.

TARIFUR R. CHOWDHURY
*Supervisory Patent Examiner*
Art Unit 2886
Technology Center 2800